US012760001B2

(12) United States Patent
Sun et al.

(10) Patent No.: US 12,760,001 B2
(45) Date of Patent: Oct. 13, 2026

(54) COMPOSITIONS AND METHODS FOR SYSTEMIC DELIVERY OF Bcl-2 AND Bcl-xL ANTAGONISTS

(71) Applicant: The Regents of the University of Michigan, Ann Arbor, MI (US)

(72) Inventors: Duxin Sun, Ann Arbor, MI (US); Wei Gao, Ann Arbor, MI (US); Hongxiang Hu, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 684 days.

(21) Appl. No.: 17/784,404

(22) PCT Filed: Dec. 11, 2020

(86) PCT No.: PCT/US2020/064530

§ 371 (c)(1),
(2) Date: Jun. 10, 2022

(87) PCT Pub. No.: WO2021/119439

PCT Pub. Date: Jun. 17, 2021

(65) Prior Publication Data

US 2023/0025865 A1 Jan. 26, 2023

Related U.S. Application Data

(60) Provisional application No. 62/958,779, filed on Jan. 9, 2020, provisional application No. 62/946,804, filed on Dec. 11, 2019.

(51) Int. Cl.

| | |
|---|---|
| ***A61K 31/337*** | (2006.01) |
| ***A61K 9/14*** | (2006.01) |
| ***A61K 31/519*** | (2006.01) |
| ***A61K 31/635*** | (2006.01) |
| ***A61K 31/675*** | (2006.01) |
| ***A61K 45/06*** | (2006.01) |
| ***A61P 35/00*** | (2006.01) |
| ***C07D 401/14*** | (2006.01) |
| *A61K 9/19* | (2006.01) |
| *A61K 47/42* | (2017.01) |

(52) U.S. Cl.

CPC .............. *C07D 401/14* (2013.01); *A61K 9/14* (2013.01); *A61P 35/00* (2018.01)

(58) Field of Classification Search

None

See application file for complete search history.

(56) References Cited

U.S. PATENT DOCUMENTS

2010/0278905 A1* 11/2010 Catron ................. A61K 9/0095 424/455
2010/0311751 A1 12/2010 Schmitt et al.
2014/0199234 A1* 7/2014 Wang ................... A61K 31/496 424/93.73

FOREIGN PATENT DOCUMENTS

WO WO 00/71079 A2 11/2000
WO WO 2017/123616 * 7/2017
WO WO 2017/132474 * 8/2017
WO WO 2021/007303 1/2021
WO WO-2021007303 A1 * 1/2021 ........... A61K 47/643

OTHER PUBLICATIONS

Golub et al. Science, vol. 286, 1999, pp. 531-537.*
Guin et al. "Lipid Metabolism Modulatory Cisplatin Prodrug Sensiszes Resistant Prostate Cancer toward Androgen Deprivation Therapy" ACS Pharmacology & Translational Science vol. 7/Issue 9 Aug. 2024.*
Song et al. "The BH3 Mimetic ABT-737 Induces Cancer Cell Senescence" Cancer Res (2011) 71 (2): 506-515.*
Pandit et al. "New otential anti-cancer agents synergize with bortezomib and ABT-737 against prostate cancer"Prostate. Jun. 1, 2010;70(8):825-833.*
M. Karimi et al., Albumin nanostructures as advanced drug delivery systems, Expert Opin Drug Deliv. Nov. 2016; 13(11): 1609-1623 (Year: 2016).*
Otagiri, Masaki et al., Albumin in Medicine, Springer Science+ Business Media Singapore, 2016, (pp. 1, and 4) (Year: 2016).*
International Search Report & Written Opinion, International Patent Application No. PCT/US2020/064530, mailed Mar. 4, 2021, 13 pages.
Bai, L et al. BM-1197: a novel and specific Bcl-2/Bcl-xL inhibitor inducing complete and long-lasting tumor regression in vivo Plos One. 2014, vol. 9 (6):e99404, 13 pages.
Bai, L. et al. BM-1252 (APG-1252): A potent dual specific Bcl-2/ Bcl-xL inhibitor that achieves complete tumor regression with minimal platelet toxicity Eur J Cancer 50, 109-110, poster (2014).
Brunsvig P F, et al., Telomerase peptide vaccination: a phase I/II study in patients with non-small cell lung cancer. Cancer Immunol Immunother. 2006;55(12): 1553-1564.

(Continued)

*Primary Examiner* — Kortney L. Klinkel
*Assistant Examiner* — Alison Azar Hastings
(74) *Attorney, Agent, or Firm* — Casimir Jones, S.C.; Robert A. Goetz

(57) ABSTRACT

This disclosure provides compositions and methods for albumin nanoformulation of Bcl-2 and Bcl-xL inhibitor APG-1252 to suppress and/or inhibit growth of cancer cells (e.g., tumor cells). In particular, the present invention is directed to compositions comprising nanoparticles associated with (e.g., complexed, conjugated, encapsulated, absorbed, adsorbed, admixed) APG-1252, methods for synthesizing such nanoparticles, as well as systems and methods utilizing such nanoparticles (e.g., in diagnostic and/or therapeutic settings). Such nanoparticle formulations of APG-1252 are capable of increasing solubility, protecting against its degradation, reducing platelet toxicity, and expanding (improving) different indications to improve anti-cancer efficacy in various cancers and cancer metastasis in lymph nodes.

6 Claims, 25 Drawing Sheets

Specification includes a Sequence Listing.

(56) References Cited

OTHER PUBLICATIONS

Kalepu, S. & Nekkanti, V. Insoluble drug delivery strategies: review of recent advances and business prospects. Acta Pharm Sin B 5, 442-453 (2015).
Li, F et al. Different nanoformulations alter the tissue distribution of paclitaxel, which aligns with reported distinct efficacy and safety profiles Mol. Pharm. Oct. 1, 2018;15(10):4505-4516.
Staehler, et al., A phase I study to evaluate safety, immunogenicity and anti-tumor activity of the multi-peptide vaccine IMA901 in renal cell carcinoma patients (RCC) ASCO meeting 2007; Journal of Clinical Oncology 25, No. 18_suppl (Jun. 20, 2007) 5098-5098.
Rudin CM et al. Phase II Study of Single-Agent Navitoclax (ABT-263) and Biomarker Correlates in Patients with Relapsed Small Cell Lung Cancer. Clin Cancer Res (2012) 18 (11): 3163-3169.

* cited by examiner

SEQUENCE LISTING

```
<160> NUMBER OF SEQ ID NOS: 16

<210> SEQ ID NO 1
<211> LENGTH: 20
<212> TYPE: PRT
<213> ORGANISM: Homo sapiens

<400> SEQUENCE: 1

Ser Cys Val Arg Ala Cys Gly Ala Asp Ser Tyr Glu Met Glu Glu Asp
1               5                   10                  15
```

```
Gly Val Arg Lys
            20


<210> SEQ ID NO 2
<211> LENGTH: 19
<212> TYPE: PRT
<213> ORGANISM: Artificial sequence
<220> FEATURE:
<223> OTHER INFORMATION: synthetic

<400> SEQUENCE: 2

Val Trp Ser Tyr Gly Val Thr Val Trp Glu Leu Met Thr Phe Gly Ser
1               5                   10                  15

Lys Pro Tyr


<210> SEQ ID NO 3
<211> LENGTH: 9
<212> TYPE: PRT
<213> ORGANISM: Artificial sequence
<220> FEATURE:
<223> OTHER INFORMATION: synthetic

<400> SEQUENCE: 3

Arg Met Phe Pro Asn Ala Pro Tyr Leu
1               5


<210> SEQ ID NO 4
<211> LENGTH: 19
<212> TYPE: PRT
<213> ORGANISM: Artificial sequence
<220> FEATURE:
<223> OTHER INFORMATION: synthetic

<400> SEQUENCE: 4

Ser Gly Gln Ala Arg Met Phe Pro Asn Ala Pro Tyr Leu Pro Ser Cys
1               5                   10                  15

Leu Glu Ser


<210> SEQ ID NO 5
<211> LENGTH: 23
<212> TYPE: PRT
<213> ORGANISM: Artificial sequence
<220> FEATURE:
<223> OTHER INFORMATION: synthetic

<400> SEQUENCE: 5

Ser Gly Gln Ala Arg Met Phe Pro Asn Ala Pro Tyr Leu Pro Ser Cys
1               5                   10                  15

Leu Glu Ser Gln Pro Thr Ile
            20


<210> SEQ ID NO 6
<211> LENGTH: 6
<212> TYPE: PRT
<213> ORGANISM: Artificial sequence
<220> FEATURE:
<223> OTHER INFORMATION: synthetic

<400> SEQUENCE: 6

Arg Pro Ala Pro Gly Ser
1               5


<210> SEQ ID NO 7
<211> LENGTH: 7
```

<212> TYPE: PRT
<213> ORGANISM: Artificial sequence
<220> FEATURE:
<223> OTHER INFORMATION: synthetic

<400> SEQUENCE: 7

Pro Pro Ala His Gly Val Thr
1               5

<210> SEQ ID NO 8
<211> LENGTH: 5
<212> TYPE: PRT
<213> ORGANISM: Artificial sequence
<220> FEATURE:
<223> OTHER INFORMATION: synthetic

<400> SEQUENCE: 8

Pro Asp Thr Arg Pro
1               5

<210> SEQ ID NO 9
<211> LENGTH: 6
<212> TYPE: PRT
<213> ORGANISM: Artificial sequence
<220> FEATURE:
<223> OTHER INFORMATION: synthetic

<400> SEQUENCE: 9

Glu Glu Val Val Ala Cys
1               5

<210> SEQ ID NO 10
<211> LENGTH: 13
<212> TYPE: PRT
<213> ORGANISM: Artificial sequence
<220> FEATURE:
<223> OTHER INFORMATION: synthetic

<400> SEQUENCE: 10

Cys Gly Tyr Gly Pro Lys Lys Lys Arg Lys Val Gly Gly
1               5                   10

<210> SEQ ID NO 11
<211> LENGTH: 5
<212> TYPE: PRT
<213> ORGANISM: Artificial sequence
<220> FEATURE:
<223> OTHER INFORMATION: synthetic

<400> SEQUENCE: 11

Asp Asp Asp Asp Asp
1               5

<210> SEQ ID NO 12
<211> LENGTH: 6
<212> TYPE: PRT
<213> ORGANISM: Artificial sequence
<220> FEATURE:
<223> OTHER INFORMATION: synthetic

<400> SEQUENCE: 12

Asp Asp Asp Asp Asp Asp
1               5

<210> SEQ ID NO 13
<211> LENGTH: 8
<212> TYPE: PRT

-continued

```
<213> ORGANISM: Artificial sequence
<220> FEATURE:
<223> OTHER INFORMATION: synthetic

<400> SEQUENCE: 13

Asn Pro Asn Ala Asn Pro Asn Ala
1               5


<210> SEQ ID NO 14
<211> LENGTH: 8
<212> TYPE: PRT
<213> ORGANISM: Artificial sequence
<220> FEATURE:
<223> OTHER INFORMATION: synthetic

<400> SEQUENCE: 14

Val Ala Ile Thr Val Leu Val Lys
1               5


<210> SEQ ID NO 15
<211> LENGTH: 6
<212> TYPE: PRT
<213> ORGANISM: Artificial sequence
<220> FEATURE:
<223> OTHER INFORMATION: synthetic

<400> SEQUENCE: 15

Val Gly Val Arg Val Arg
1               5


<210> SEQ ID NO 16
<211> LENGTH: 5
<212> TYPE: PRT
<213> ORGANISM: Artificial sequence
<220> FEATURE:
<223> OTHER INFORMATION: synthetic

<400> SEQUENCE: 16

Val Pro Asp Pro Arg
1               5
```

COMPOSITIONS AND METHODS FOR SYSTEMIC DELIVERY OF Bcl-2 AND Bcl-xL ANTAGONISTS

CROSS-REFERENCE TO RELATED APPLICATIONS

The present application is a U.S. 371 National Entry of PCT/US2020/064530, filed Jun. 10, 2022, which claims priority to U.S. Provisional Patent Application Ser. No. 62/946,804 filed Dec. 11, 2019 and U.S. Provisional Patent Application Ser. No. 62/958,779, filed Jan. 9, 2020 which are hereby incorporated by reference in their entireties.

SEQUENCE LISTING

The text of the computer readable sequence listing filed Dec. 11, 2020, titled "37926-601_ST25" created Dec. 11, 2020, having a file size of 3,434 bytes, is hereby incorporated by reference in its entirety.

FIELD OF THE INVENTION

This disclosure provides compositions and methods for albumin nanoformulation of Bcl-2 and Bcl-xL inhibitor APG-1252 to suppress and/or inhibit growth of cancer cells (e.g., tumor cells). In particular, the present invention is directed to compositions comprising nanoparticles associated with (e.g., complexed, conjugated, encapsulated, absorbed, adsorbed, admixed) APG-1252, methods for synthesizing such nanoparticles, as well as systems and methods utilizing such nanoparticles (e.g., in diagnostic and/or therapeutic settings). Such nanoparticle formulations of APG-1252 are capable of increasing solubility, protecting against its degradation, reducing platelet toxicity, and expanding (improving) different indicaions to improve anti-cancer efficacy in various cancers and cancer metastasis in lymph nodes.

BACKGROUND OF THE INVENTION

Bcl-2 family proteins play pivotal roles in regulating programmed cell death, or apoptosis (see, Bai, L. et al. Eur J Cancer 50, 109-110 (2014)). Dual Bcl-2 and Bcl-xL inhibitor shows promising efficacy in treating solid tumor, but its application hindered by on-target toxicity of platelets that occurs during Bcl-xL inhibition. APG-1252

( 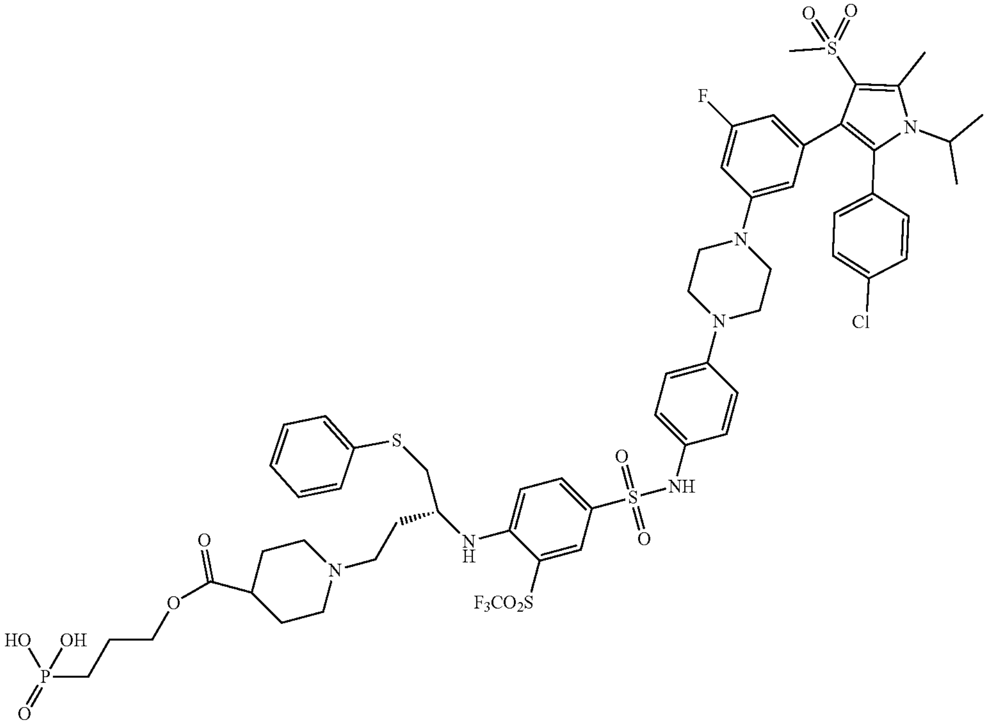 )

((R)-(3-((1-(3-((4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-((trifluoromethyl)sulfonyl)phenyl)amino)-4-(phenylthio)butyl) piperidine-4-carbonyl)oxy)propyl)phosphonic acid) is designed as a prodrug by adding a phosphate lipid to BM-1244

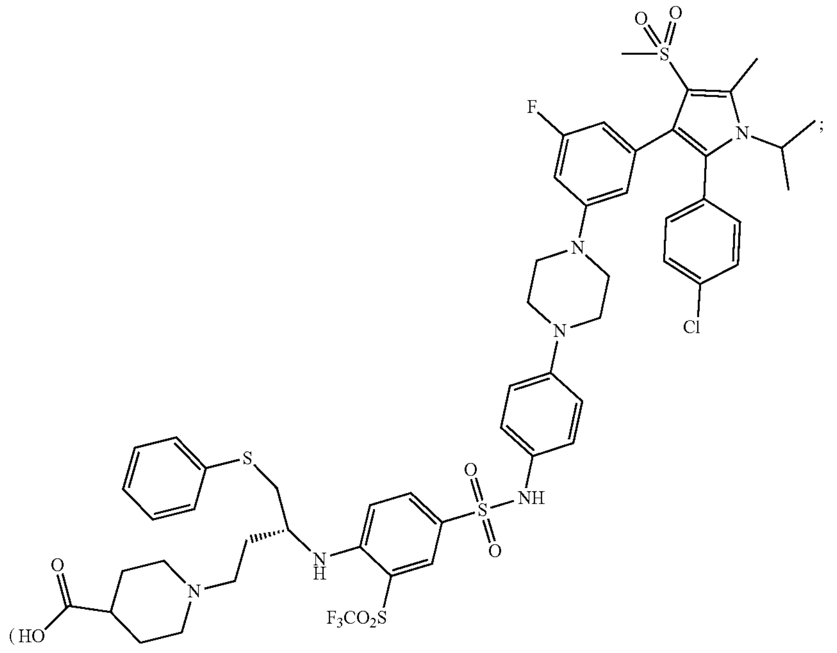

(R)-1-(3-((4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-((trifluoromethyl) sulfonyl)phenyl)amino)-4-(phenylthio)butyl)piperidine-4-carboxylic acid), a potent Bcl-2 and Bcl-xL dual inhibitor, to overcome toxicity that may occur during Bcl-xL inhibition, while maintaining strong anti-tumor potency (see, Bai, L. et al. Eur J Cancer 50, 109-110 (2014)). Preclinical studies have shown that APG-1252 alone achieves complete and persistent tumor regression in multiple tumor xenograft models with a twice weekly or weekly dose-schedule, including small cell lung cancer (SCLC), colon, breast and acute lymphoblastic leukemia (ALL) cancer xenografts; achieves strong synergy with the chemotherapeutic agents, indicating that APG-1252 may have a broad therapeutic potential for the treatment of human cancer as a single agent or in combination with other classes of anticancer drugs (see, Bai, L. et al. Eur J Cancer 50, 109-110 (2014)). APG-1252 has been advanced into Phase 1 clinical trials for the treatment of patients with SCLC or other solid tumors.

There are several potential limitations for the use of APG-1252 in broad spread clinical applications. First, APG-1252 is a phosphate prodrug, which limit the drug uptake into the platelet to reduce toxicity. However, in order to exhibit strong anticancer efficacy of APG-1252, the active form BM-1244 need to be released in tumor site and maintain anti-tumor potency by cleavage of an unstable ester bond in APG-1252 (see, BM-1197: a novel and specific Bcl-2/Bcl-xL inhibitor inducing complete and long-lasting tumor regression in vivo. Bai, L et al. Plos One. 2014). However, BM-1244 can be prematurely released in the circulation by the hydrolysis of ester bond in circulation, which will cause platelet toxicity and limit dose escalation in clinical use.

Second, the unstable ester bond of APG-1252 is very challenging to maintain its stability during during manufacture and storage condition. These conditions needs to be strictly controlled to maintain the very low percentage of BM-1244 in the formulation. The slightly increased hydrolyzed product BM-1244 during manufacture and storage increase the risk of platelet toxicity.

Third, APG-1252 has poor aqueous solubility that is difficult to formulate in clinical formulations. In order to reach the clinical dosing concentration (minimal 10 mg/ml) for i.v injection, the traditional way is to use a high percentage of co-solvents or surfactant, such as polyoxyethylated castor oil, ethanol, polyethyleneglycol (PEG) (see, Kalepu, S. & Nekkanti, V. Acta Pharm Sin B 5, 442-453 (2015)). However, these co-solvents or surfactant are associated with toxicity or infusion reaction in patients, especially when used in high dose. For instance, TAXOL®, an intravenous injection of paclitaxel, is the most debated formulation using this approach. Each mL of sterile nonpyrogenic solution contains 6 mg paclitaxel, 527 mg of purified CREMOPHOR EL® (polyoxyethylated castor oil) and 49.7% (v/v) dehydrated alcohol. A severe hypersensitivity reaction is observed in patient owing to the highcontent of CREMOPHOR EL®, thus all patients should be pretreated with antihistamines.

Fourth, the polarity of phosphates in the APG-1252 limits its tissue targeting and distribution, which potentially limits its clinical indication in various solid cancers.

The APG-1252 has limited distribution in bone marrow, lymph node and spleen, which potentially limits its clinical indication in hematological malignancies, such as lymphoblastic or lymphocytic cancers (including acute lymphoblastic leukemia, chronic lymphocytic leukemia, lymphomas, etc), myelogenous or myeloid cancers (including acute myelogenous leukemia, chronic myelogenous leukemia, multiple myeloma, myelodysplastic syndromes and the myeloproliferative neoplasms, such as essential thrombocythemia, polycythemia vera and myelofibrosis).

Fifth, any inhibitors of BCL2/BCL-XL is unlikely to be used as single agent in cancer therapy. The combination of BCL2/BCL-XL inhibitors with other chemotherapeutic drugs are required. The co-delivery nanoformulation of two class of drugs will improve their efficacy.

Accordingly, improved formulations of APG-1252 are needed to solve the above-mentioned problems.

The present invention addresses this need.

SUMMARY

Nanoformulations have become a well-established approach to improve efficacy and reduce toxicity of drugs. Experiments conducted during the course of developing embodiments for the present invention synthesized an albumin nanoformulation of APG-1252 (HSA-1252) with or without other chemotherapeutic drugs. The size of the nanoformulation was shown to be capable of being tuned between 50-200 nm by changing the manufacture process parameter. The lyophilization process was optimized. The size distribution, zeta potential, drug concentration was characterized before and after lyophilization. The stability of the formulation was observed including the stability in solution, the dilution stability and long-term stability in storage. In addition, the platelet toxicity were evaluated in animal models. Further, the anticancer efficacy were performed in tumor cells to demonstrate the equivalence of antitumor efficacy between nanoformulation and free drug.

Accordingly, such results and embodiments indicate a new class of drug delivery systems for both local and systemic delivery of small molecular antagonists of Bcl-2 and Bcl-xL proteins (e.g., APG-1252).

As such, this disclosure provides compositions and methods for inhibiting Bcl-2 and Bcl-xL protein activity in cancerous cells with APG-1252 to suppress and/or inhibit growth of such cancer cells (e.g., tumor cells). In particular, the present invention is directed to compositions comprising nanoparticles associated with (e.g., complexed, conjugated, encapsulated, absorbed, adsorbed, admixed) APG-1252, methods for synthesizing such nanoparticles, as well as systems and methods utilizing such nanoparticles (e.g., in diagnostic and/or therapeutic settings).

Accordingly, in certain embodiments, the present invention provides compositions comprising a nanoparticle associated with (e.g., complexed, conjugated, encapsulated, absorbed, adsorbed, admixed) APG-1252.

In some embodiments, such a nanoparticle comprises albumin associated with (e.g., complexed, conjugated, encapsulated, absorbed, adsorbed, admixed) APG-1252. In some embodiments, the concentration of APG-1252 within such nanoparticles (e.g., albumin associated with APG-1252) is approximately 10-15 mg/mL (e.g., 5-20 mg/mL; 6-19 mg/mL; 7-18 mg/mL; 8-17 mg/mL; 9-16 mg/mL). In some embodiments, the size of such nanoparticles (e.g., albumin associated with APG-1252) is approximately 50-200 nm (e.g., 40-210 nm; 45-205 nm; 60-190 nm; 70-180 nm; 100-150 nm; etc).

Experiments conducted during the course of developing embodiments of the present invention determined that the albumin nano-formulation APG-1252 formed a very stable nano shell outside of APG-1252, which remained stable in circulation. This firmly bounded albumin nano shell reduced the platelet toxicity of APG-1252 by the following mechanisms (1) reduce concentration in the blood circulation, (2) decrease platelet uptake, (3) protect premature degradation of APG-1252 in circulation.

Such experiments further determined that the albumin nano-formulation APG-1252 increased stability of APG-1252 during manufacture and storage conditions. The percentage of hydrolysis product BMS-1244 was well controlled, and no other related substance was detected. The firmly bounded albumin nano shell may slow down the hydrolysis of APG-1252 and extend shelf life of the formulation Such experiments further determined that the albumin nano-formulation APG-1252 increased solubility of APG-1252. The solubility of APG-1252 was able to be largely increased and meet the clinical dosing requirement for 10-15 mg/ml. Without the addition of surfactant, which induce hypersensitivity reaction in clinic, the albumin formulation showed better safety comparing to the present formulation.

Such experiments further determined that the albumin nano-formulation APG-1252 will improve anticancer efficacy and expand the clinical indication in different types of cancers. The albumin nano-formulation APG-1252 have preference in tissue targeting and enhance tissue distribution in various organs, which will have better efficacy in the targeted organs with residual tumors. The potential use for these for preferred tissue targeting can be expanded for treatment of lymphoma, cancer arised from bone marrow and blood cancer, cancers metastasis in lymph nodes, breast cancer, lung cancer, pancreatic cancer, kidney cancer, gastric cancer and GI cancer, and sarcoma.

Such experiments further determined that the albumin nano-formulation APG-1252 will improve anticancer efficacy and expand the clinical indication in hematological malignancies or bone marrow disease. The albumin nano-formulation APG-1252 is capable of increasing the accumulation in bone marrow, lymph node and spleen. The potential use for these for such preferred tissue targeting can be expanded for treatment of hematological malignancies, such as lymphoblastic or lymphocytic cancers (including acute lymphoblastic leukemia, chronic lymphocytic leukemia, lymphomas, etc), myelogenous or myeloid cancers (including acute myelogenous leukemia, chronic myelogenous leukemia, multiple myeloma, myelodysplastic syndromes and the myeloproliferative neoplasms, such as essential thrombocythemia, polycythemia vera and myelofibrosis).

Such experiments further determined that the albumin nano-formulation APG-1252 can be formulated with other chemotherapeutic drugs (such as, e.g., Paclitaxel, deocetaxel, and any other chemotherapeutics) in one nanoformulations, which can serve as co-delivery of different drugs into cancer cells. This will improve clinical efficacy.

Accordingly, in certain embodiments, the present invention provides methods for treating cancer in a subject, the method comprising administering a pharmaceutically effective amount of a composition comprising one or more nanoparticles associated with an agent capable of inhibiting Bcl-2 and Bcl-xL protein activity in at least one cancer cell from the subject.

In some embodiments, the agent capable of inhibiting Bcl-2 and Bcl-xL protein activity in at least one cancer cell from the subject is APG-1252. The agent capable of inhibiting Bcl-2 and Bcl-xL protein activity in at least one cancer cell from the subject is not limited to only APG-1252. Indeed, any agent capable of inhibiting Bcl-2 and Bcl-xL protein activity in at least one cancer cell from the subject is APG-1252 can be associated with a nanoparticle for purposes described herein. For example, other selective BCL-2/xl inhibitors or BCL-2 family inhibitors can be encapsulated into albumin nanoparticle to diminish the platelet toxicity and increase antitumor efficacy, such as BM-1244, ABT-737, ABT-263, ABT-199, A-1155463, Chelerythrine chloride, Dehydrocorydaline chloride, S55746, WEHI-539 hydrochloride, Gossypol, TW-37, A-385358, (R)-(−)-Gossypol acetic acid, AZD4320, Dehydrocorydaline, HA14-1, BH3I-1, (R)-(−)-Gossypol, (S)-Gossypol acetic acid, Navitoclax-piperazine, MCL-1/BCL-2-IN-1, MCL-1/BCL-2-IN-3, Bcl-2-IN-2, BAD (103-127), (+)-Apogossypol, desmorpholinyl Navitoclax-NH-Me, an orally available BCL-XL selective inhibitor A-1331852, XZ739 (a CRBN-dependent PROTAC BCL-XL degrader), PROTAC Bcl2 degrader-1, and other BCL-2 family inhibitor, such as pan-bcl-2 inhibitor Sabutoclax, Obatoclax Mesylate, as well as MCL-1 inhibitor S63845, AZD-5991, (R)-MIK665 (a special Mel-1 inhibitor), AMG-176, MIK665, A-1210477, Maritoclax, UMI-77, ML311 and PROTAC Mcll degrader-1, Thevetiaflavone, MCL-I/BCL-2-IN-2, and Pyridoclax.

Such methods are not limited to a particular manner of administration. In some embodiments, the administration is systemic administration.

In some embodiments, the composition is co-administered with a chemotherapeutic agent. In some embodiments, the chemotherapeutic agent is one or more of the following: aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (TAXOL®), pilocarpine, prochloroperazine, rituximab, tamoxifen, taxol, topotecan hydrochloride, trastuzumab, vinblastine, vincristine and vinorelbine tartrate.

In some embodiments, the nanoparticle associated with APG-1252 is further associated with (e.g., complexed, conjugated, encapsulated, absorbed, adsorbed, admixed) with one or more agents configured to target cancer cells.

In some embodiments, the agent configured to target cancer cells is a tumor antigen selected from the group consisting of alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGS), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68KP1, C0-029, FGF-5, G250, Ga733 (EpCAM), human EGFR protein or its fragments, such as human EGFR residues 306-325 (SCVRACGADSYEMEEDGVRK (SEQ ID NO: 1)) and residues 897-915 (VWSYGVTVWELMTFGSKPY (SEQ ID NO: 2)), HTgp-175, M344, MA-50, MG7-Ag, MOV18, NB70\K, NY-CO-1, RCAS1, SDCCAG16, TA-90 (Mac-2 binding protein\cyclophilin C-associated protein), TAAL6, TAG72, TLP, TPS, WT1 (and WT1-derivaed peptide sequences: WT1 126-134 (RMFP NAPYL (SEQ ID NO: 3)), WT1 122-140 (SGQARMFPNAPYLPSCLES (SEQ ID NO: 4)), and WT1 122-144 (SGQARMFPNAPYLPSCLESQPTI (SEQ ID NO: 5)), MUC1 (and MUC1-derived peptides and glycopeptides such as RPAPGS (SEQ ID NO: 6), PPAHGVT (SEQ ID NO: 7), and PDTRP (SEQ ID NO: 8)), LMP2, EGFRvIII, Idiotype, GD2, Ras mutant, p53 mutant, Proteinase3 (PR1), Survivin, hTERT, Sarcoma translocation breakpoints, EphA2, EphA4, LMW-PTP, PAP, ML-IAP, AFP, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, sLe(animal), CYP1B1, PLAC1, GM3, BORIS, Tn, GloboH, NY-BR-1, RGS5, SART3, STn, Carbonic anhydrase IX, PAX5, OY-TES1, Sperm protein 17, LCK, HMWMAA, AKAP-4, XAGE 1, B7H3, Legumain, Tie 2, Page4, VEGFR2, MAD-CT-1, FAP, PDGFR-alpha, PDGFR-β, MAD-CT-2, Fos-related antigen 1, ERBB2, Folate receptor 1 (FOLR1 or FBP), IDH1, IDO, LY6K, fms-related tyrosine kinase 1 (FLT1, best known as VEGFR1), KDR, PADRE, TA-CIN (recombinant HPV16 L2E7E6), SOX2, aldehyde dehydrogenase, and any derivative thereof.

In some embodiments, the one or more agents configured to target cancer cells are conjugated to the outer surface of the nanoparticle. In some embodiments, the one or more agents configured to target cancer cells are encapsulated within the nanoparticle.

Additional embodiments will be apparent to persons skilled in the relevant art based on the teachings contained herein.

DEFINITIONS

Figure 1:
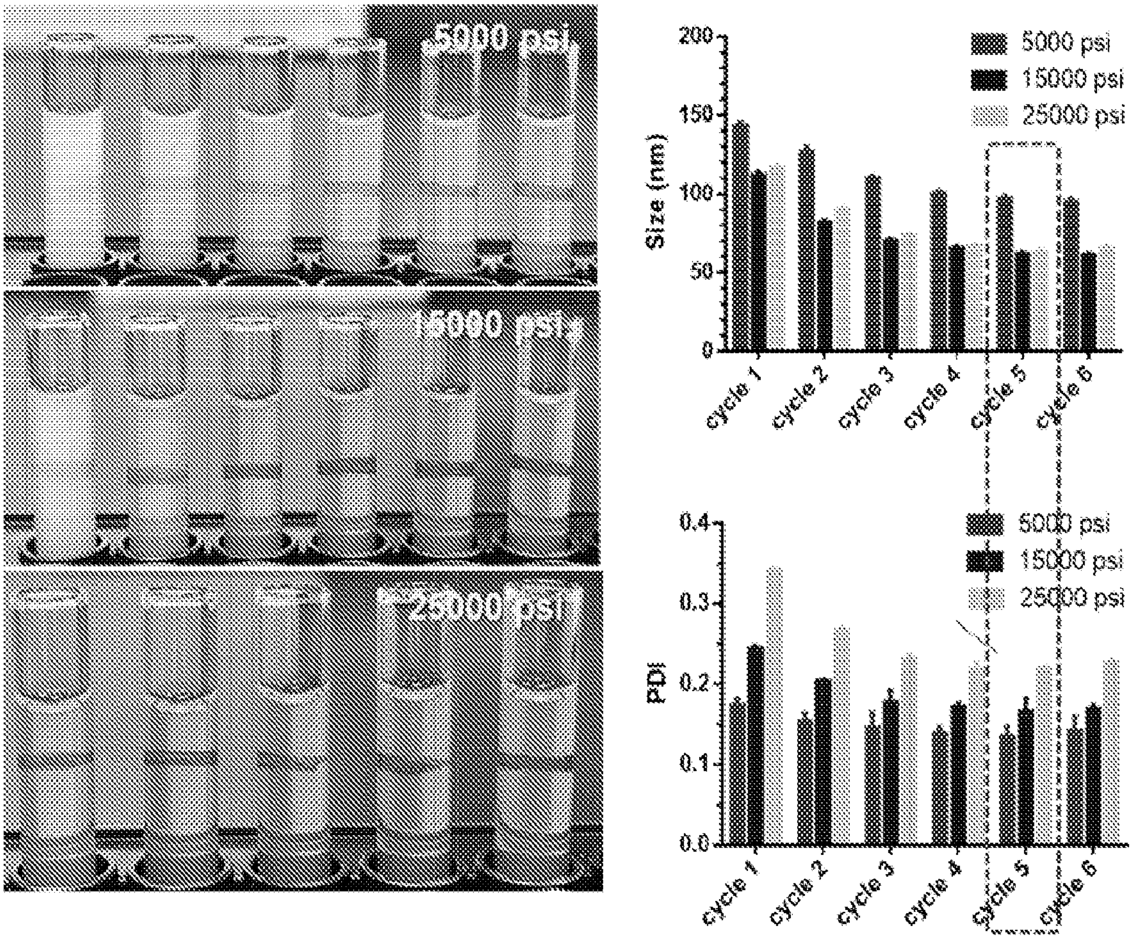
FIG. 1. The size distribution of HSA-1252 varies with different cycle and pressure used in high-pressure homogenizer.

To facilitate an understanding of the present invention, a number of terms and phrases are defined below:

As used herein, the term "complexed" as used herein relates to the non-covalent interaction of a biomacromolecule agent (e.g., antigen, adjuvant, etc) with a nanoparticle and/or microparticle.

As used herein, the term "conjugated" as used herein indicates a covalent bond association between a a biomacromolecule agent (e.g., antigen, adjuvant, etc) and a nanoparticle and/or microparticle.

As used herein, the term "encapsulated" refers to the location of a biomacromolecule agent (e.g., antigen, adjuvant, etc) that is enclosed or completely contained within the inside of a nanoparticle and/or microparticle.

As used herein, the term "absorbed" refers to a biomacromolecule agent (e.g., antigen, adjuvant, etc) that is taken into and stably retained in the interior, that is, internal to the outer surface, of a nanoparticle and/or microparticle.

As used herein, the term "adsorbed" refers to the attachment of a biomacromolecule agent (e.g., antigen, adjuvant, etc) to the external surface of a nanoparticle and/or microparticle.

Such adsorption preferably occurs by electrostatic attraction. Electrostatic attraction is the attraction or bonding generated between two or more oppositely charged or ionic chemical groups. Generally, the adsorption is typically reversible.

As used herein, the term "admixed" refers to a biomacromolecule agent (e.g., antigen, adjuvant, etc) that is dissolved, dispersed, or suspended in a nanoparticle and/or microparticle. In some cases, the biomacromolecule agent may be uniformly admixed in the nanoparticle and/or microparticle.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

DETAILED DESCRIPTION OF THE INVENTION

Impaired apoptosis is one of the hallmarks of cancer and contributes to tumor progression and resistance to conventional cancer therapy. One of the main apoptosis pathways is the mitochondria-mediated intrinsic pathway, which is defined by mitochondrial outer membrane permeabilization (MOMP). On the molecular level, MOMP is controlled by the dynamic interactions between a set of pro-apoptotic and anti-apoptotic B cell lymphoma-2 (Bcl-2) proteins. Proteins of the anti-apoptotic Bcl-2 family, including Bcl-2, Bcl-xL, Bcl-w, Mel-1, and Bfl1/A1, inhibit MOMP by sequestering pro-apoptotic Bcl-2 family members, such as Bax, Bak, Bim, Bid, and Puma (see, BM-1197: a novel and specific Bcl-2/Bcl-xL inhibitor inducing complete and long-lasting tumor regression in vivo. Bai, L et al. Plos One. 2014).

BCL-2 has shown to have a dominant role in the survival of multiple lymphoid malignancies. ABT-199 (Venetoclax), a selectively Bcl-2 inhibitor has been proved to treat chronic lymphocytic leukemia. However, it doesn't work in solid tumor. BCL-XL was subsequently identified as a related prosurvival protein and is associated with drug resistance and disease progression of multiple solid-tumor and hematological malignancies. Dual Bcl-2 and Bcl-xL target inhibitor is promising in treating solid tumor. ABT-263, one of the dual Bcl-2 and Bcl-xL target inhibitor, have proven to be promising in clinical trials for relapsed small cell lung cancer, refractory or relapsed lymphoid malignancies, and other solid tumors (see, Phase II study of single-agent navitoclax (ABT263) and biomarker correlates in patients with relapsed small cell lung cancer. RudinCM et al. Clin Cancer Res. 2012). However, BCL-XL is also the primary survival factor in platelets. Pharmacologic inhibition of BCL-XL results in reduced platelet half-life and dose-dependent thrombocytopenia in vivo. The platelet toxicity is the major hurdle for the clinical application of dual Bcl-2 and Bcl-xL inhibitor.

BM-1244 is a potent Bcl-2 and Bcl-xL dual inhibitor. APG-1252 is a prodrug of BM-1244, designed to overcome on-target toxicity of platelets by adding phosphate lipid to block the binding to Bcl-xl. In order to make the active form BM-1244 release in tumor site and maintain anti-tumor potency, an unstable ester bond is used to make the prodrug (see, BM-1197: a novel and specific Bcl-2/Bcl-xL inhibitor inducing complete and long-lasting tumor regression in vivo. Bai, L et al. Plos One. 2014). This strategy reduces the side effect in some extend and moving to a Phase I/II clinical trial. However, due to the unstable ester bond, part of BM-1244 will still release in circulation and cause the side effect, which limited the dose used in clinic. On the other hand, it requires precisely controlled the BM-1244 percentage of the product during manufacture and storage. Only −20 degree can be used for storage to reduce the hydrolysis, that makes very difficult for clinical application. As a result, there is a need to further reduce the platelet toxicity of APG-1252 for clinic use.

Experiments conducted during the course of developing embodiments for present invention developed an albumin nano-formulation of APG-1252 (HSA-1252). The albumin nano-formulation formed a very stable nano shell outside of APG-1252, which remains stable and integrated in circulation. This firmly bounded albumin nano shell reduced the platelet toxicity of APG-1252. HSA-1252 showed no obvious platelet depletion at the conc of 50 mg/Kg, while clinic used formulation induce significant platelet depletion. This enhancement was possibly due to the decreased platelet uptake or blood retention time of the APG-1252 and the reduced hydrolysis of the drug.

On the other hand, the solubility of APG-1252 was able to be largely increased and meet the clinical dosing requirement for 10-15 mg/ml by albumin nanoformulation. Most importantly, albumin formulation avoids the hypersensitivity reaction of surfactant which used commonly in formulations to increase the solubility.

The size of the nanoparticle was shown to be tunable in the range of 50 to 200 nm with a narrow size distribution (PDI <0.15). The nanoformulation was shown to be stable during the lypophilization process, and the same size distribution maintained after resuspension from lypophilization powder. Finally, the long term stability studies demonstrated HSA-1252 is stable during 6 month storage. HSA-1252 had a slightly higher hydrolysis rate compared to clinical-1252, but remained in acceptable range for at least 13 months. Clinical-1252 introduces a new impurity due to the drug and expients reaction, which may induce potential risk in patients. Due to the narrow size distribution and in vitro stability, the HSA-1252 shows a high potential of clinical translation.

Accordingly, this disclosure provides compositions and methods for inhibiting Bcl-2 and Bcl-xL protein activity in cancerous cells with APG-1252 to suppress and/or inhibit growth of such cancer cells (e.g., tumor cells). In particular, the present invention is directed to compositions comprising nanoparticles associated with (e.g., complexed, conjugated, encapsulated, absorbed, adsorbed, admixed) APG-1252, methods for synthesizing such nanoparticles, as well as systems and methods utilizing such nanoparticles (e.g., in diagnostic and/or therapeutic settings).

The albumin nanoformulations can also co-encapsulate other therapeutic agents or drugs with APG-1252, which are able to co-deliver the agents to target tissues for synergitic therapeutic effect or reducing the toxicity.

The present invention is not limited to specific types or kinds of nanoparticles associated with (e.g., complexed, conjugated, encapsulated, absorbed, adsorbed, admixed) APG-1252 configured for treating, preventing or ameliorating various types of disorders (e.g., cancer).

In certain embodiments, the nanoparticle utilized is an albumin nanoformulation associated with APG-1252.

Additional examples of nanoparticles include, but are not limited to, fullerenes (a.k.a. $C_{60}$, $C_{70}$, $C_{76}$, $C_{80}$, $C_{84}$), endohedral metallofullerenes (EMI's) buckyballs, which contain additional atoms, ions, or clusters inside their fullerene cage), trimetallic nitride templated endohedral metallofullerenes (TNT EMEs, high-symmetry four-atom molecular cluster endohedrals, which are formed in a trimetallic nitride template within the carbon cage), single-walled and mutli-walled carbon nanotubes, branched and dendritic carbon nanotubes, gold nanorods, silver nanorods, single-walled and multi-walled boron/nitrate nanotubes, carbon nanotube peapods (nanotubes with internal metallo-fullerenes and/or other internal chemical structures), carbon nanohorns, carbon nanohorn peapods, liposomes, nanoshells, dendrimers, quantum dots, superparamagnetic nanoparticles, nanorods, and cellulose nanoparticles. The particle embodiment can also include microparticles with the capability to enhance effectiveness or selectivity. Other non-limiting exemplary nanoparticles include glass and polymer micro- and nano-spheres, biodegradable PLGA micro- and nano-spheres, gold, silver, carbon, and iron nanoparticles.

Additional examples of nanoparticles include, by way of example and without limitation, paramagnetic nanoparticles, superparamagnetic nanoparticles, metal nanoparticles, fullerene-like materials, inorganic nanotubes, dendrimers, dendrimers with covalently attached metal chelates, nanofibers, nanohorns, nano-onions, nanorods, nanoropes and quantum dots. In some embodiments, a nanoparticle is a metal nanoparticle (for example, a nanoparticle of gold, palladium, platinum, silver, copper, nickel, cobalt, iridium, or an alloy of two or more thereof). Nanoparticles can include a core or a core and a shell, as in core-shell nanoparticles.

In certain embodiments, the present invention provides a composition comprising a nanoparticle (e.g., albumin) associated with (e.g., complexed, conjugated, encapsulated, absorbed, adsorbed, admixed) one or more small molecular antagonists of Bcl-2 and Bcl-xL protein activity in cancerous cells.

Such compositions are not limited to particular small molecular antagonists of Bcl-2 and Bcl-xL. In some embodiments, the small molecule antagonist of Bcl-2 and Bcl-xL is APG-1252.

In certain embodiments, the present invention provides compositions comprising a nanoparticle (e.g., albumin) associated with one or more antagonists of Bcl-2 and Bcl-xL protein activity in cancerous cells (e.g., APG-1252), wherein any kind of biomacromolecule agent (e.g., nucleic acid, peptides, glycolipids, etc.) is further associated with (e.g., complexed, conjugated, encapsulated, absorbed, adsorbed, admixed) the nanoparticle.

In some embodiments, the biomacromolecule agent is a peptide.

For example, in some embodiments, the peptide is an antigen.

In some embodiments, the antigen is a tumor antigen. The antigen can be a tumor antigen, including a tumor-associated or tumor-specific antigen, such as, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGS), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68KP1, C0-029, FGF-5, G250, Ga733 (EpCAM), human EGFR protein or its fragments, such as human EGFR residues 306-325 (SCVRACGADSYEMEEDGVRK (SEQ ID NO: 1)) and residues 897-915 (VWSYGVTVWELMTFGSKPY (SEQ ID NO: 2)), HTgp-175, M344, MA-50, MG7-Ag, MOV18, NB70\K, NY-CO-1, RCAS1, SDCCAG16, TA-90 (Mac-2 binding protein\cyclophilin C-associated protein), TAAL6, TAG72, TLP, TPS, WT1 (and WT1-derivaed peptide sequences: WT1 126-134 (RMFP NAPYL (SEQ ID NO: 3)), WT1 122-140 (SGQARMFPNAPYLPSCLES (SEQ ID NO: 4)), and WT1 122-144 (SGQARMFPNAPYLPSCLESQPTI (SEQ ID NO: 5)), MUC1 (and MUC1-derived peptides and glycopeptides such as RPAPGS (SEQ ID NO: 6), PPAHGVT (SEQ ID NO: 7), and PDTRP (SEQ ID NO: 8))), LMP2, EGFRvIII, Idiotype, GD2, Ras mutant, p53 mutant, Proteinase3 (PR1), Survivin, hTERT, Sarcoma translocation breakpoints, EphA2, EphA4, LMW-PTP, PAP, ML-IAP, AFP, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, sLe(animal), CYP1B1, PLAC1, GM3, BORIS, Tn, GloboH, NY-BR-1, RGS5, SART3, STn, Carbonic anhydrase IX, PAX5, OY-TES1, Sperm protein 17, LCK, HMWMAA, AKAP-4, XAGE 1, B7H3, Legumain, Tie 2, Page4, VEGFR2, MAD-CT-1, FAP, PDGFR-alpha, PDGFR-β, MAD-CT-2, Fos-related antigen 1, ERBB2, Folate receptor 1 (FOLR1 or FBP), IDH1, IDO, LY6K, fms-related tyrosine kinase 1 (FLT1, best known as VEGFR1), KDR, PADRE, TA-CIN (recombinant HPV16 L2E7E6), SOX2, and aldehyde dehydrogenase.

In some embodiments wherein the biomacromolecule is a peptide. In some embodiments, the peptide is Adrenocorticotropic Hormone (ACTH), a growth hormone peptide, a Melanocyte Stimulating Hormone (MSH), Oxytocin, Vasopressin, Corticotropin Releasing Factor (CRF), a CRF-related peptide, a Gonadotropin Releasing Hormone Associated Peptide (GAP), Growth Hormone Releasing Factor (GRF), Lutenizing Hormone Release Hormone (LH-RH), an orexin, a Prolactin Releasing Peptide (PRP), a somatostatin, Thyrotropin Releasing Hormone (THR), a THR analog, Calcitonin (CT), a CT-precursor peptide, a Calcitonin Gene Related Peptide (CGRP), a Parathyroid Hormone (PTH), a Parathyroid Hormone Related Protein (PTHrP), Amylin, Glucagon, Insulin, an Insulin-like peptide, NeuroPeptide Y (NPY), a Pancreatic Polypeptide (PP), Peptide YY (PYY), Cholecystokinin (CCK), a CCK-related peptide, Gastrin Releasing Peptide (GRP), Gastrin, a Gastrin-related peptide, a Gastrin inhibitory peptide, Motilin, Secretin, Vasoactive Intestinal Peptide (VIP), a VIP-related peptide, an Atrial-Natriuretic Peptide (ANP), a Brain Natriuretic Peptide (BNP), a C-Type Natriuretic Peptide(CNP), a tachykinin, an angiotensin, a renin substrate, a renin inhibitor, an endothelin, an endothelin-related peptide, an opioid peptide, a thymic peptide, an adrenomedullin peptide, an allostatin peptide, an amyloid beta-protein fragment, an antimicrobial peptide, an antioxidant peptide, an apoptosis related peptide, a Bag Cell Peptide (BCPs), Bombesin, a bone Gla protein peptide, a Cocaine and Amphetamine Related Transcript (CART) peptide, a cell adhesion peptide, a chemotactic peptide, a complement inhibitor, a cortistatin peptide, a fibronectin fragment, a fibrin related peptide, FMRF, a FMRF amide-related peptide (FaRP), Galanin, a Galanin-related peptide, a growth factor, a growth factor-related peptide, a G-Therapeutic Peptide-Binding Protein fragment, Gualylin, Uroguanylin, an Inhibin peptide, Interleukin (IL), an Interleukin Receptor protein, a laminin fragment, a leptin fragment peptide, a leucokinin, Pituitary Adenylate Cyclase Activating Polypeptide (PAPCAP), Pancreastatin, a polypeptide repetitive chain, a signal transducing reagent, a thrombin inhibitor, a toxin, a trypsin inhibitor, a virus-related peptide, an adjuvant peptide analog, Alpha Mating Factor, Antiarrhythmic Peptide, Anorexigenic Peptide, Alpha-1 Antitrypsin, Bovine Pineal Antireproductive Peptide, Bursin, C3 Peptide P16, Cadherin Peptide, Chromogranin A Fragment, Contraceptive Tetrapeptide, Conantokin G, Conantokin T, Crustacean Cardioactive Peptide, C-Telopeptide, Cytochrome b588 Peptide, Decorsin, Delicious Peptide, Delta-Sleep-Inducing Peptide, Diazempam-Binding Inhibitor Fragment, Nitric Oxide Synthase Blocking Peptide, OVA Peptide, Platelet Calpain Inhibitor (P1), Plasminogen Activator Inhibitor 1, Rigin, Schizophrenia Related Peptide, Sodium Potassium Atherapeutic Peptidase Inhibitor-1, Speract, Sperm Activating Peptide, Systemin, a Thrombin receptor agonist, Tuftsin, Adipokinetic Hormone, Uremic Pentapeptide, Antifreeze Polypeptide, Tumor Necrosis Factor (TNF), Leech [Des Asp10]Decorsin, L-Ornithyltaurine Hydrochloride, P-Aminophenylacetyl Tuftsin, Ac-Glu-Glu-Val-Val-Ala-Cys-Pna (SEQ ID NO: 9), Ac-Ser-Asp-Lys-Pro, Ac-rfwink-NH2, Cys-Gly-Tyr-Gly-Pro-Lys-Lys-Lys-Arg-Lys-Val-Gly-Gly (SEQ ID NO: 10), D-Ala-Leu, D-D-D-D-D (SEQ ID NO: 11), D-D-D-D-D-D (SEQ ID NO: 12), N-P-N-A-N-P-N-A (SEQ ID NO: 13), V-A-I-T-V-L-V-K (SEQ ID NO: 14), V-G-V-R-V-R (SEQ ID NO: 15), V-I-H-S, V-P-D-P-R (SEQ ID NO: 16), Val-Thr-Cys-Gly, R-S-R, Sea Urchin Sperm Activating Peptide, a SHU-9119 antagonist, a MC3-R antagonist, a MC4-R antagonist, Glaspimod, HP-228, Alpha 2-Plasmin Inhibitor, APC Tumor Suppressor, Early Pregnancy Factor, Gamma Interferon, Glandular Kallikrei N-1, Placental Ribonuclease Inhibitor, Sarcolecin Binding Protein, Surfactant Protein D, Wilms' Tumor Suppressor, GABAB 1b Receptor Peptide, Prion Related Peptide (iPRP13), Choline Binding Protein Fragment, Telomerase Inhibitor, Cardiostatin Peptide, Endostatin Derived Peptide, Prion Inhibiting Peptide, N-Methyl D-Aspartate Receptor Antagonist, and C-PeptideAnalog.

In some embodiments, the peptide is selected from 177Lu-DOTA0-Tyr3-Octreotate, Abarelix acetate, ADH-1, Afamelanotidec, melanotan-1, CUV1647, Albiglutide, Aprotinin, Argipressin, Atosiban acetate, Bacitracin, Bentiromide, a BH3 domain, Bivalirudin, Bivalirudin trifluoroacetate hydrate, Blisibimod, Bortezomib, Buserelin, Buserelin acetate, Calcitonin, Carbetocin, Carbetocin acetate, Cecropin A and B, Ceruletide, Ceruletide diethylamine, Cetrorelix, Cetrorelix acetate, Ciclosporine, Cilengitidec, EMD121974, Corticorelin acetate injection, hCRF, Corticorelin ovine triflutate, corticorelin trifluoroacetate, Corticotropin, Cosyntropin, ACTH 1-24, tetracosactide hexaacetate, Dalbavancin, Daptomycin, Degarelix acetate, Depreotide trifluoroacetate (plus sodium pertechnetate), Desmopressin acetate, Desmopressin DDAVP, Dulaglutide, Ecallantide, Edotreotide (plus yttrium-90), Elcatonin acetate, Enalapril maleate (or 2-butanedioate), Enfuvirtide, Eptifibatide, Exenatide, Ganirelix acetate, Glatiramer acetate, Glutathion, Gonadorelin, Gonadorelin acetate, GnRH, LHRH, Goserelin, Goserelin acetate, Gramicidin, Histrelin acetate, Human calcitonin, Icatibant, Icatibant acetate, IM862, oglufanide disodium, KLAKLAK, Lanreotide acetate, Lepirudin, Leuprolide, Leuprolide acetate, leuprorelin, Liraglutide, Lisinopril, Lixisenatide, Lypressin, Magainin2, MALP-2Sc, macrophage-activating lipopeptide-2 synthetic, Nafarelin acetate, Nesiritide, NGR-hTNF, Octreotide acetate, Oritavancin, Oxytocin, Pasireotide, Peginesatide, Pentagastrin, Pentetreotide (plus indium-111), Phenypressin, Pleurocidin, Pramlintide, Protirelin, thyroliberin, TRH, TRF, Salmon calcitonin, Saralasin acetate, Secretin (human), Secretin (porcine), Semaglutide, Seractide acetate, ACTH, corticotropin, Sermorelin acetate, GRF 1-29, Sinapultide, KL4 in lucinactant, Sincalide, Somatorelin acetate, GHRH, GHRF, GRF, Somatostatin acetate, Spaglumat magnesium (or sodium) salt, Substance P, Taltirelin hydrate, Teduglutide, Teicoplanin, Telavancin, Teriparatide, Terlipressin acetate, Tetracosactide, Thymalfasin, thymosin a-1, Thymopentin, Trebananib, Triptorelin, Triptorelin pamoate, Tyroserleutide, Ularitide, Vancomycin, Vapreotide acetate, Vasoactive intestinal peptide acetate, Vx-001c, TERT572Y, Ziconotide acetate, $\alpha$5-$\alpha$6 Bax peptide, and $\beta$-defensin.

In some embodiments, the peptide is any peptide which would assist in achieving a desired purpose with the composition. For example, in some embodiments, the peptide is any peptide that will facilitate treatment of any type of disease and/or disorder (e.g., cancer).

In some embodiments, the biomacromolecule agent is a nucleic acid. Such embodiments encompass any type of nucleic acid molecule including, but not limited to, RNA, siRNA, microRNA, interference RNA, mRNA, replicon mRNA, RNA-analogues, and DNA.

According to the invention, the above-described nanoformulations (e.g., albumin associated with APG-1252) may be used for a patient that has been diagnosed as having cancer, or at risk of developing cancer, through administering the nanoformulation to the patient in a therapeutically effective manner. In one embodiment, the patient may have a solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas.

The nanoformulations (e.g., albumin associated with APG-1252) can be administered alone or in combination with other therapeutic agents. The therapeutic agent is for example, a chemotherapeutic or biotherapeutic agent, radiation, or immunotherapy. Any suitable therapeutic treatment for a particular cancer may be administered. Examples of chemotherapeutic and biotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (TAXOL®), pilocarpine, prochloroperazine, rituximab, tamoxifen, taxol, topotecan hydrochloride, trastuzumab, vinblastine, vincristine and vinorelbine tartrate. For prostate cancer treatment, a preferred chemotherapeutic agent with which anti-CTLA-4 can be combined is paclitaxel (TAXOL®).

The optimum amount of such nanoformulations (e.g., albumin associated with APG-1252) to be included and the optimum dosing regimen can be determined by one skilled in the art without undue experimentation. For example, the nanoformulations (e.g., albumin associated with APG-1252) may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c, i.d., i.p., i.m., and i.v. Preferred methods of DNA injection include i.d., i.m., s.c, i.p. and i.v. For example, doses of between 1 and 500 mg 50 μg and 1.5 mg, preferably 10 μg to 500 μg, of peptide or DNA may be given and will depend from the respective peptide or DNA. Doses of this range were successfully used in previous trials (Brunsvig P F, et al., Cancer Immunol Immunother. 2006; 55(12): 1553-1564; M. Staehler, et al., ASCO meeting 2007; Abstract No 3017). Other methods of administration of the vaccine composition are known to those skilled in the art.

In certain embodiments, the nanoformulations (e.g., albumin associated with APG-1252) as described herein are further associated with (e.g., complexed, conjugated, encapsulated, absorbed, adsorbed, admixed) one or more therapeutic agents. Such embodiments are not limited to particular type or kind of therapeutic agent.

In some embodiments, the therapeutic agent configured for treating and/or preventing cancer. Examples of such therapeutic agents include, but are not limited to, chemotherapeutic agents, anti-oncogenic agents, anti-angiogenic agents, tumor suppressor agents, anti-microbial agents, etc.

In some embodiments, the therapeutic agent is configured for treating and/or preventing autoimmune disorders and/or inflammatory disorders. Examples of such therapeutic agents include, but are not limited to, disease-modifying antirheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), glucocorticoids (e.g., prednisone, methylprednisone), TNF-$\alpha$ inhibitors (e.g., adalimumab, certolizumab pegol, etanercept, golimumab, infliximab), IL-1 inhibitors, and metalloprotease inhibitors. In some embodiments, the therapeutic agents include, but are not limited to, infliximab, adalimumab, etanercept, parenteral gold or oral gold.

In some embodiments, the therapeutic agent is configured for treating and/or preventing cardiovascular related disorders (e.g., atherosclerosis, heart failure, arrhythmia, atrial fibrillation, hypertension, coronary artery disease, angina pectoris, etc.). Examples of therapeutic agents known to be useful in treating and/or preventing cardiovascular related disorders include, angiotensin-converting enzyme (ACE) inhibitors (e.g., benazepril, enalapril, Lisinopril, perindopril, Ramipril), adenosine, alpha blockers (alpha adrenergic antagonist medications) (e.g., clonidine, guanabenz, labetalol, phenoxybenzamine, terazosin, doxazosin, guanfacine, methyldopa, prazosin), angtiotensin II receptor blockers (ARBs) (e.g., candesartan, irbesartan, olmesartan medoxomil, telmisartan, eprosartan, losartan, tasosartan, valsartan), antiocoagulants (e.g., heparin fondaparinux, warfarin, ardeparin, enoxaparin, reviparin, dalteparin, nadroparin, tinzaparin), antiplatelet agents (e.g., abciximab, clopidogrel, eptifibatide, ticlopidine, cilostazol, dipyridamole, sulfinpyrazone, tirofiban), beta blockers (e.g., acebutolol, betaxolol, carteolol, metoprolol, penbutolol, propranolol, atenolol, bisoprolol, esmolol, nadolol, pindolol, timolol), calcium channel blockers (e.g., amlopidine, felodipine, isradipine, nifedipine, verapamil, diltiazem, nicardipine, nimodipine, nisoldipine), diuretics, aldosterone blockers, loop diuretics (e.g., bumetanide, furosemide, ethacrynic acid, torsemide), potassium-sparing diuretics, thiazide diuretics (e.g., chlorothiazide, chlorthalidone, hydrochlorothiazide, hydroflumethiazide, methyclothiazide, metolazone, polythiazide, quinethazone, trichlormethiazide), inoptropics, bile acid sequestrants (e.g., cholestyramine, coletipol, colesevelam), fibrates (e.g., clofibrate, gemfibrozil, fenofibrate), statins (e.g., atorvastatinm, lovastatin, simvastatin, fluvastatin, pravastatin), selective cholesterol absorption inhibitors (e.g., ezetimibe), potassium channel blockers (e.g., amidarone, ibutilide, dofetilide), sodium channel blockers (e.g., disopyramide, mexiletine, procainamide, quinidine, flecainide, moricizine, propafenone), thrombolytic agents (e.g., alteplase, reteplase, tenecteplase, anistreplase, streptokinase, urokinase), vasoconstrictors, vasodilators (e.g., hydralazine, minoxidil, mecamylamine, isorbide dintrate, isorbide mononitrate, nitroglycerin).

Generally, the nanoparticles so formed are spherical and have a diameter of from about 40 to 200 nm (e.g., 30-220 nm; 35-215 nm; 45-190 nm; 55 to 180 nm; 75-150 nm; 90 to 130 nm; 100-110 nm; etc.). In some embodiments, the nanoformulations (e.g., albumin associated with APG-1252) are subjected to size exclusion chromatography to yield a more homogeneous preparation.

In some embodiments, the nanoformulations (e.g., albumin associated with APG-1252) as described herein are further associated with (e.g., complexed, conjugated, encapsulated, absorbed, adsorbed, admixed) agents useful for determining the location of administered particles. Agents useful for this purpose include fluorescent tags, radionuclides and contrast agents.

Suitable imaging agents include, but are not limited to, fluorescent molecules such as those described by Molecular Probes (Handbook of fluorescent probes and research products), such as Rhodamine, fluorescein, Texas red, Acridine Orange, Alexa Fluor (various), Allophycocyanin, 7-aminoactinomycin D, BOBO-1, BODIPY (various), Calcien, Calcium Crimson, Calcium green, Calcium Orange, 6-carboxyrhodamine 6G, Cascade blue, Cascade yellow, DAPI, DiA, DID, Dil, DiO, DiR, ELF 97, Eosin, ER Tracker Blue-White, EthD-1, Ethidium bromide, Fluo-3, Fluo4, FM1-43, FM4-64, Fura-2, Fura Red, Hoechst 33258, Hoechst 33342, 7-hydroxy-4-methylcoumarin, Indo-1, JC-1, JC-9, JOE dye, Lissamine rhodamine B, Lucifer Yellow CH, LysoSensor Blue DND-167, LysoSensor Green, LysoSensor Yellow/Blu, Lysotracker Green FM, Magnesium Green, Marina Blue, Mitotracker Green FM, Mitotracker Orange CMTMRos, MitoTracker Red CMXRos, Monobromobimane, NBD amines, NeruoTrace 500/525 green, Nile red, Oregon Green, Pacific Blue. POP-1, Propidium iodide, Rhodamine 110, Rhodamine Red, R-Phycoerythrin, Resorfin, RH414, Rhod-2, Rhodamine Green, Rhodamine 123, ROX dye, Sodium Green, SYTO blue (various), SYTO green (Various), SYTO orange (various), SYTOX blue, SYTOX green, SYTOX orange, Tetramethylrhodamine B, TOT-1, TOT-3, X-rhod-1, YOYO-1, YOYO-3. In some embodiments, ceramides are provided as imaging agents. In some embodiments, SiP agonists are provided as imaging agents.

Additionally, radionuclides can be used as imaging agents. Suitable radionuclides include, but are not limited to radioactive species of Fe(III), Fe(II), Cu(II), Mg(II), Ca(II), and Zn(II) Indium, Gallium and Technetium. Other suitable contrast agents include metal ions generally used for chelation in paramagnetic T1-type MIR contrast agents, and include di- and tri-valent cations such as copper, chromium, iron, gadolinium, manganese, erbium, europium, dysprosium and holmium. Metal ions that can be chelated and used for radionuclide imaging, include, but are not limited to metals such as gallium, germanium, cobalt, calcium, indium, iridium, rubidium, yttrium, ruthenium, yttrium, technetium, rhenium, platinum, thallium and samarium. Additionally metal ions known to be useful in neutron-capture radiation therapy include boron and other metals with large nuclear cross-sections. Also suitable are metal ions useful in ultrasound contrast, and X-ray contrast compositions.

Examples of other suitable contrast agents include gases or gas emitting compounds, which are radioopaque.

In some embodiments, the nanoformulations (e.g., albumin associated with APG-1252) as described herein are further associated with (e.g., complexed, conjugated, encapsulated, absorbed, adsorbed, admixed) a targeting agent. In some embodiments, targeting agents are used to assist in delivery of the nanoformulations (e.g., albumin associated with APG-1252) as described herein to desired body regions. Examples of targeting agents include, but are not limited to, an antibody, receptor ligand, hormone, vitamin, and antigen, however, the present invention is not limited by the nature of the targeting agent. In some embodiments, the antibody is specific for a disease-specific antigen. In some embodiments, the receptor ligand includes, but is not limited to, a ligand for CFTR, EGFR, estrogen receptor, FGR2, folate receptor, IL-2 receptor, glycoprotein, and VEGFR. In some embodiments, the receptor ligand is folic acid.

In some embodiments, the present invention also provides kits comprising nanoformulations (e.g., albumin associated with APG-1252) as described herein. In some embodiments, the kits comprise one or more of the reagents and tools necessary to generate such nanoformulations, and methods of using such nanoformulations.

The nanoformulations (e.g., albumin associated with APG-1252) as described herein may be characterized for size and uniformity by any suitable analytical techniques. These include, but are not limited to, atomic force microscopy (AFM), electrospray-ionization mass spectroscopy, MALDI-TOF mass spectroscopy, $^{13}C$ nuclear magentic resonance spectroscopy, high performance liquid chromatography (HPLC) size exclusion chromatography (SEC) (equipped with multi-angle laser light scattering, dual UV and refractive index detectors), capillary electrophoresis and get electrophoresis. These analytical methods assure the uniformity of the nanoformulation (e.g., albumin associated with APG-1252) population and are important in the production quality control for eventual use in in vivo applications.

In some embodiments, gel permeation chromatography (GPC) is used to analyze the nanoformulations (e.g., albumin associated with APG-1252). In some embodiments, the size distribution and zeta-potential is determined by dynamic light scattering (DLS) using, for example, a Malven Nanosizer instrument.

Where clinical applications are contemplated, in some embodiments of the present invention, the nanoformulations (e.g., albumin associated with APG-1252) are prepared as part of a pharmaceutical composition in a form appropriate for the intended application. Generally, this entails preparing compositions that are essentially free of pyrogens, as well as other impurities that could be harmful to humans or animals.

In some embodiments, the nanoformulations (e.g., albumin associated with APG-1252) as described herein are used in conjunction with appropriate salts and buffers to render delivery of the compositions in a stable manner to allow for uptake by target cells. Buffers may also be employed when the nanoformulations (e.g., albumin associated with APG-1252) are introduced into a patient. Aqueous compositions comprise an effective amount of the nanoformulations to cells dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with the vectors or cells of the present invention, its use in therapeutic compositions is contemplated. Supplementary active ingredients may also be incorporated into the compositions.

In some embodiments of the present invention, the active compositions include classic pharmaceutical preparations. Administration of these compositions according to the present invention is via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection.

The active nanoformulations (e.g., albumin associated with APG-1252) as described herein may also be administered parenterally or intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Additional formulations that are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%-2%. Vaginal suppositories or pessaries are usually globular or oviform and weighing about 5 g each. Vaginal medications are available in a variety of physical forms, e.g., creams, gels or liquids, which depart from the classical concept of suppositories. The nanoformulations (e.g., albumin associated with APG-1252) also may be formulated as inhalants.

The present invention also includes methods involving co-delivery or co-administration of the nanoformulations (e.g., albumin associated with APG-1252) as described herein with one or more additional active agents. Indeed, it is a further aspect of this invention to provide methods for enhancing prior art therapies and/or pharmaceutical compositions by co-administering the nanoformulations (e.g., albumin associated with APG-1252) of this invention with such additional active agents. In co-administration procedures, the agents may be administered concurrently or sequentially. In some embodiments, the nanoformulations (e.g., albumin associated with APG-1252) described herein are administered prior to the other active agent(s). The agent or agents to be co-administered depends on the type of condition being treated.

Experimental

The following examples are provided in order to demonstrate and further illustrate certain preferred embodiments and aspects of the present invention and are not to be construed as limiting the scope thereof.

Example 1

This example describes the materials and methods for Examples II-VI.

Chemicals and Reagents.

APG-1252 and BM-1244 was given by Ascentage Pharma (Jiangsu, China). Albumin (Human) U.S.P. ALBUTEIN® 5% was purchased from Grifols Biologicals Inc. (LosAngeles, USA). High performance liquid chromatography (HPLC) grade acetonitrile was purchased from Sigma-Aldrich (St Louis, MO, USA) and HPLC column (XBRIDGE® C18 3.5 μm) was from Waters (Massachusetts, USA). Ultrapure deionized water was obtained using a Milli-Q water system (Millipore, Bedford, MA, USA). Sodium chloride injections (0.9%) were purchased from Hospira Inc. (Lake Forest, IL, USA). CellTiter 96™ AQueous Nonradioactive Cell Proliferation Assay Kit was purchased from PROMEGA® (Madison, WI, United States).

The Preparation of the HSA-1252

Organic phase was prepared by dissolving the 1252 (200 mg) into chloroform (2 ml). 20 ml Marketed HSA solution (5%) is then mixed with organic phase and dispersed vigorously by a rotor-stator homogenizer (Ultra-Turrax T25, 8K rpm-12K rpm, 5 min) to generate milk-like emulsion. The emulsion was then processed by a high-pressure homogenizer (Nano DeBEE) with the parameters set as pressure=15,000 psi-20,000 psi, condensation temp=5° C., cycles=6. Remaining organic solvent in the product was removed by a rotatory evaporator. The final nano-suspension was filtered with 0.22 μm membrane, and then directly put into 10 ml vials (2 ml/vial) for lyophilization (primary drying temp=−5° C. for 30 h and secondary drying temp=30° C. for 6 h). The vials were filled with nitrogen before sealing and stored at −20° C.

The Characterization of HSA-1252

The size distribution and zeta potential was determined by dynamic light scattering (DLS) using Malvern Zetasizer Nano ZS. The APG-1252 concentration in nanoformulation was determined by HPLC. Simply, HSA-1252 formulation was diluted with acetonitrile (1:4 v/v), sonicated for 10 mins and centrifugated under 4° C. for 15 mins with 10,000 rpm. The APG-1252 concentration in the supernatant was analyzed by HPLC with the water mobile phase set as phosphate buffer with pH as 3.5±0.1) and organic mobile phase using acetonitrile. Agilent C18 column (150 mm×4.6 mm, 3.5 μm) is used for the separation and the detection wavelength is set at 254 nm.

The Optimization of Lyophilization Process of HSA-1252

Primary drying temperature during the lyophilization process was optimized. The thermal treatment was fixed as 5° C. for 30 min and −40° C. for 1 h. Three different temperature points (−10° C., 0° C., 10° C.) were set for the primary drying process and last for 10 h under 150 mTorr vacuum. Secondary drying temperature was fixed as 30° C. for 4 h. The real formulation temperature was monitored by a thermo detector.

Resuspension of Lyophilized Powder

The lyophilized powder of both HSA-1252 and clinical used formulation (clinical-1252) was resuspended with different medium, including water, saline and PBS.

The Stability of APG-1252 During Formulation Preparation and Lyophilization Process.

The contents of APG-1252 and its hydrolysis product BM-1244 were measured before and after formulation preparation and lyophilization process by method described above.

The Storage Stability Evaluation of HSA-1252 Lyophilized Powder

Different vials of HSA-1252 lyophilized powder were put at −20° C., 4° C. and 25° C. At each sampling time point (0 month, 1 month, 3 month, 6 month), the vials were taken and suspended with sodium chloride injections (0.9%) for a drug concentration of 10 mg/ml. Then, the APG-1252 contents and size distribution were measured.

Example II

This example describes the preparation and characterization of the HSA-1252 formulation.

The HSA-1252 was successfully prepared. The final concentration of APG-1252 in formulation can be reached to 10-15 mg/mL, which meets the requirement of i.v dosing in clinic.

As shown in FIG. 1, by changing the pressure and cycle used in high-pressure homogenizer, the average size of the nanoparticle can be tuned from 56 to 180 nm, and a narrow size distribution can be obtained with PDI <0.15. After lyophilization, the size distribution and zeta potential were not changed.

Figure 2:
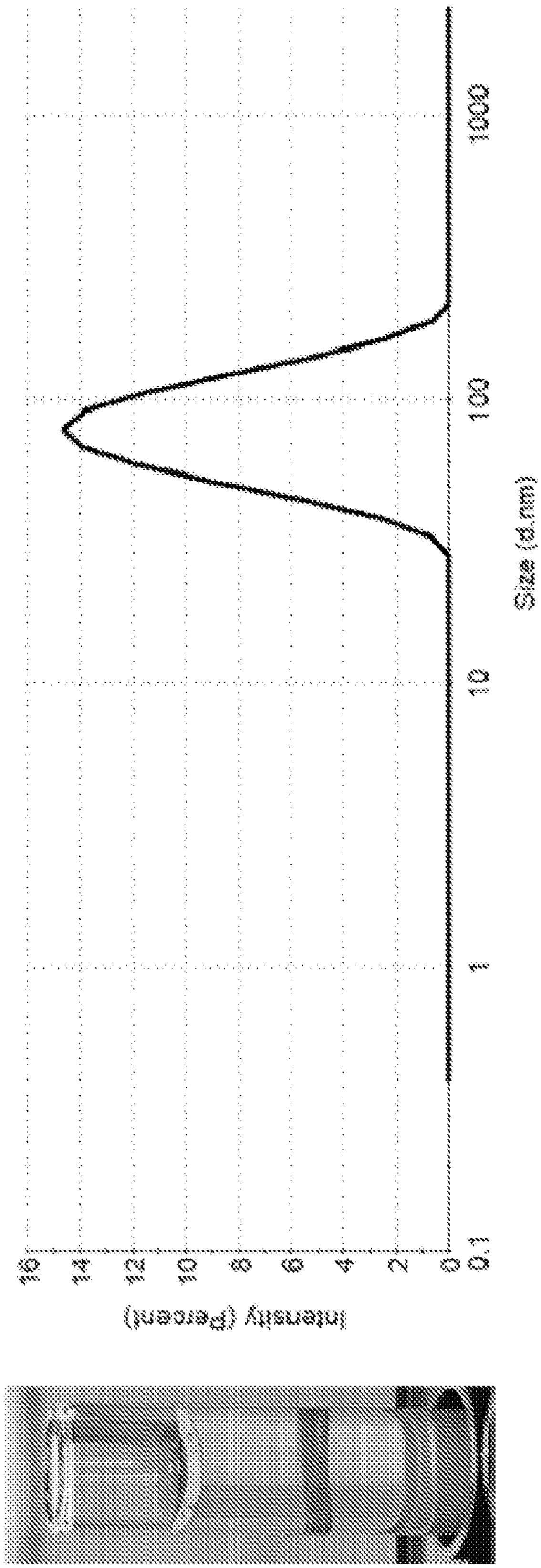
FIG. 2. The appearance and size distribution of optimized HSA-1252 formulation.

The characterization of one optimized formulation is shown in FIG. 2. The formulation suspension was clear with minor blue light, and no big precipitate was observed. The z-average size was 72.28±0.318 nm, PDI was 0.135±0.003, zeta potential was −20.67±1.17 mV.

Example III

This example describes the lyophilization process optimization and lyophilization product characterization of the HSA-1252 formulation.

Figure 3:
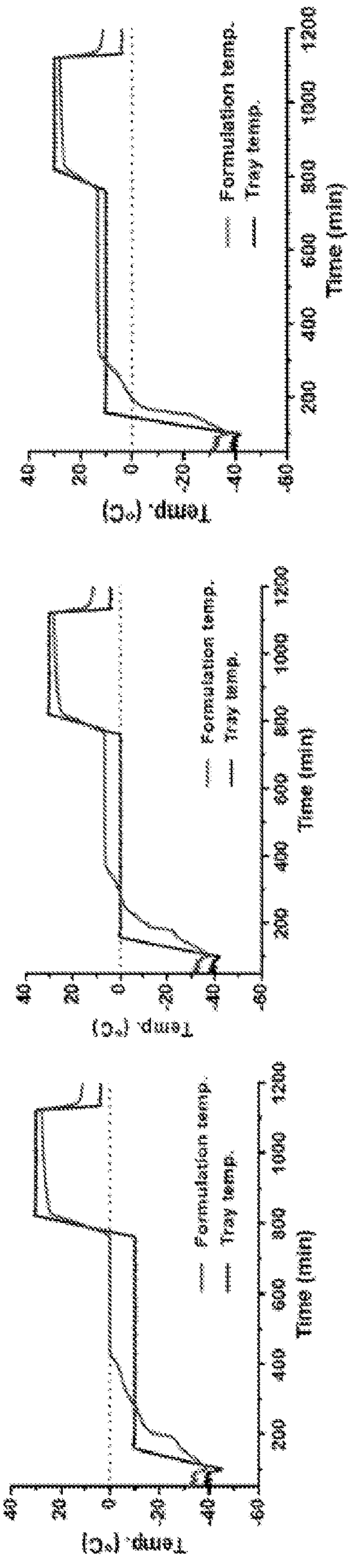
FIG. 3. The impact of different parameters in lyophilization process

The lyophilization process of HSA-1252 was optimized by changing the primary drying temperature (−10° C., 0° C., 10° C.). As shown in FIG. 3, along with the increase of tray temperature, the formulation took less time for freeze-drying. Even though 'cake' form generated in all cases, abrupt temperature increase did happen in the case with drying temperature set as 10° C.

Figure 4:
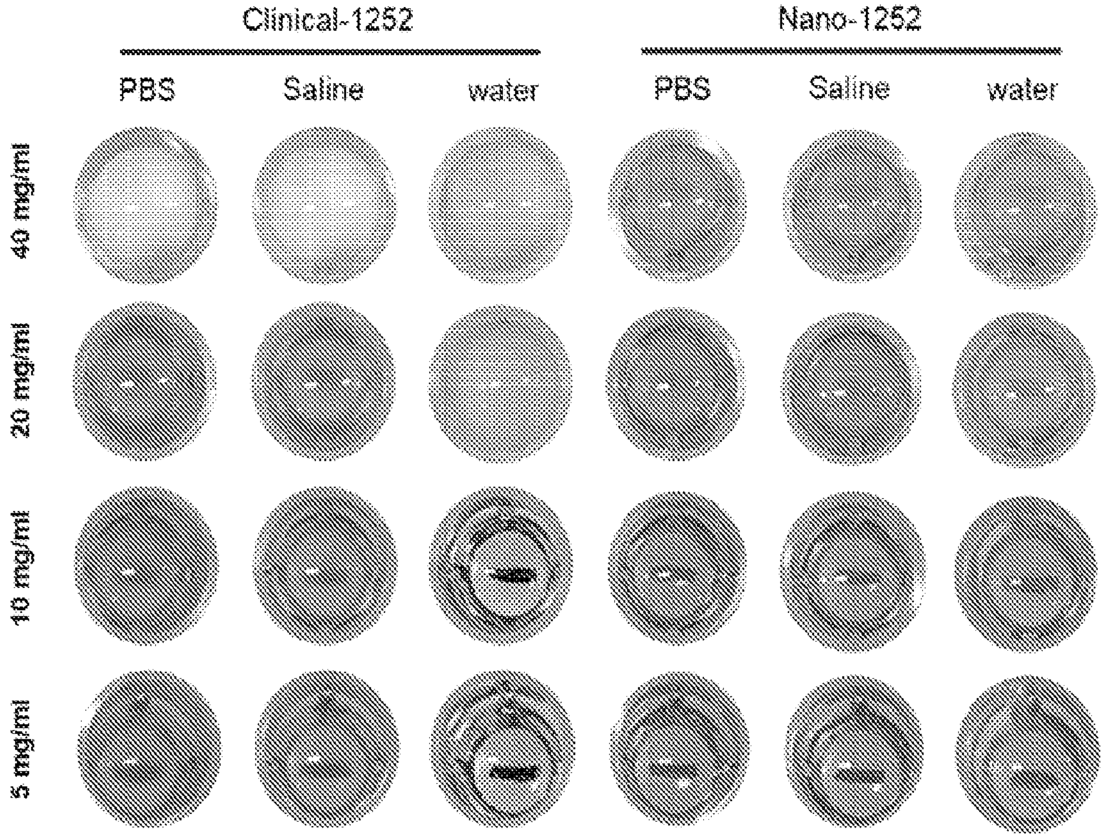
FIG. 4. The appearance of Nano-1252 and clinical used formulation clinical-1252 in PBS, saline and water.

The lyophilization powder of HSA-1252 has short resuspention time for within 1 min in different medium (water, saline and PBS). As shown in FIG. 4, the apprearance of HSA-1252 after resuspension is transparant with slightly blue light. Comparing to the nanoformulation, the clinical used formulation has longer resuspention time, and cannot be well resuspended at high concentration. The apprearance of clincial-1252 is not transparent.

Example IV

This example describes the stability of HSA-1252 during the preparation and lyophilization process.

Since APG-1252 is not stable and can be hydrolyzed to BM-1244 in water, the percentage of BM-1244 is controlled during the preparation and lyophilization process. After optimization the procedure, no obvious increase of 1244 was observed in the final lyophilization product (0.176%) compared to original drug (0.16%). No other new impurities were detected based on HPLC analysis.

Example V

This example describes the formulation stability of HSA-1252 lypholization powder.

Figure 5:
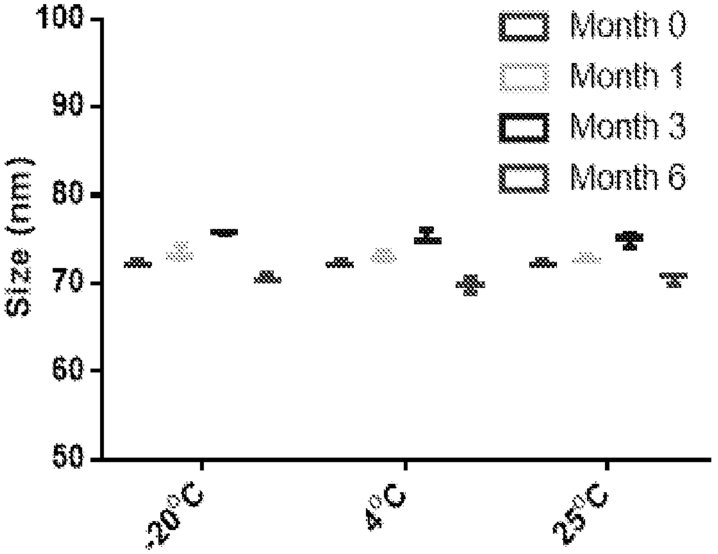
FIG. 5. Formulation stability of HSA-1252 during long-term storage analyzed with average particle size (left) and distribution/PDI.
Figure 5:
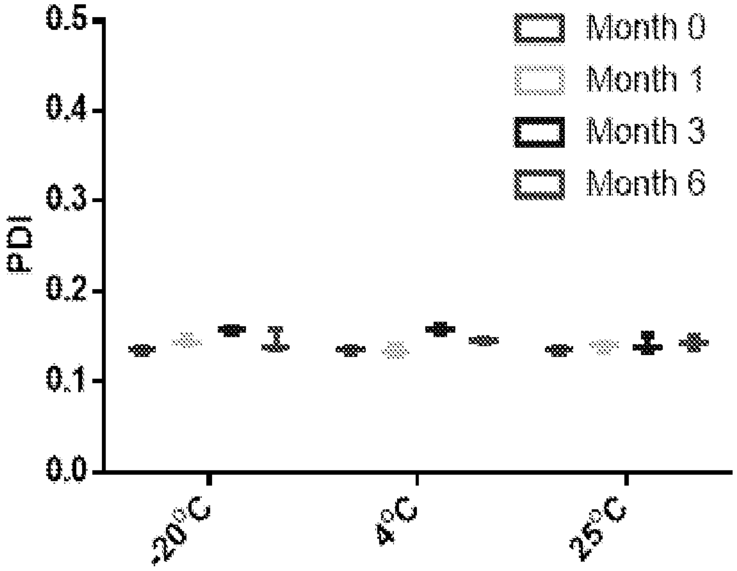

HSA-1252 lypholization powder were storaged at −20, 4, 25° C. for 6 monthes. The size distribution after resuspention was observed. As shown in FIG. 5, neither z-average nor PDI has no significant changes at all the three temperatures. These results demonstrated that the lypholization powder is stable during storage for 6 monthes.

Example VI

This example describes the long-term chemical stability of HSA-1252 lyophilized powder.

Figure 6:
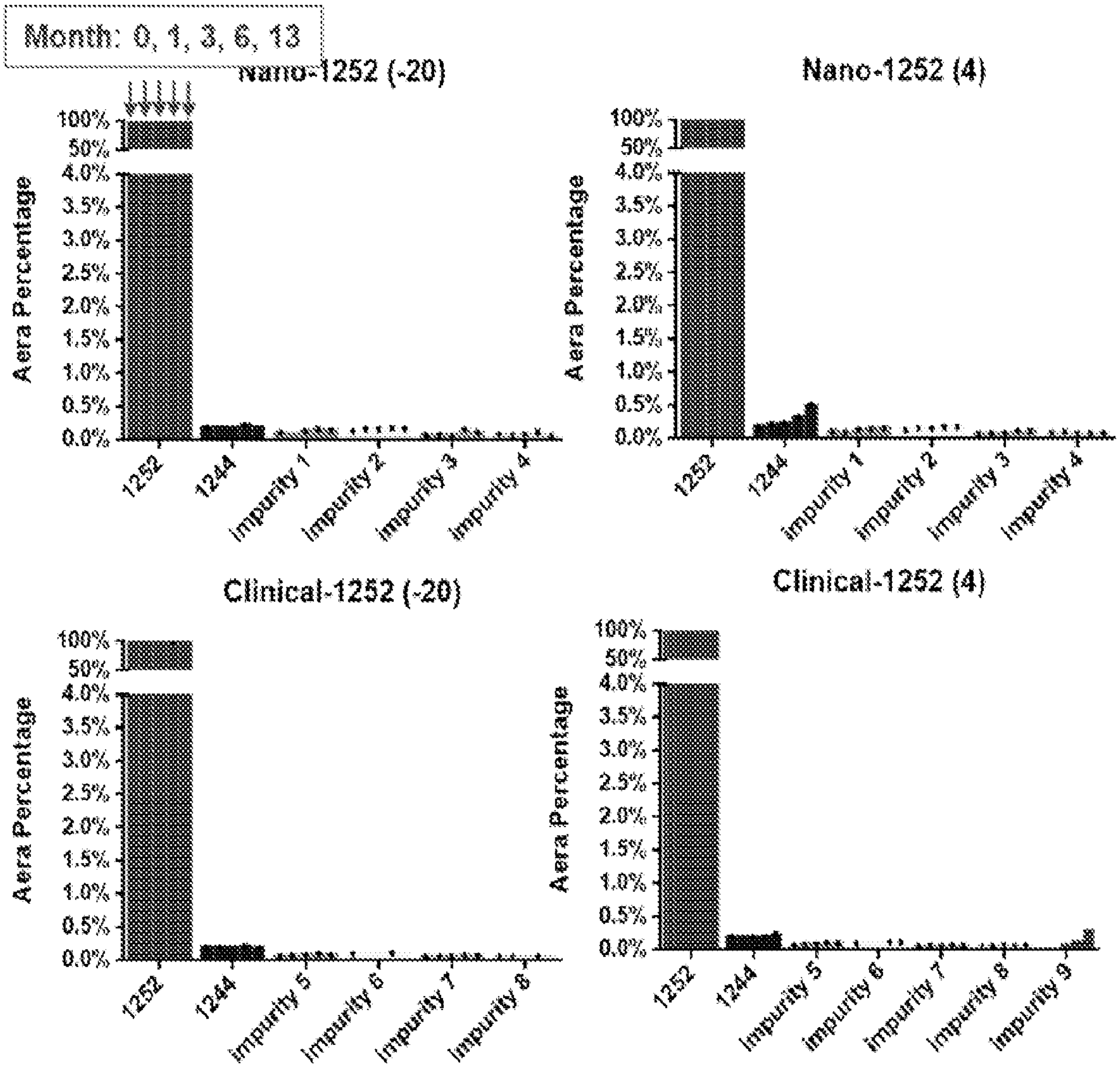
FIG. 6. APG-1252 chemical stability during long-term storage analyzed by HP.

The long-term storage stability study of HSA-1252 and clinical formulation lyophilized powder was measured at −20° C. and 4° C. for 13 months. As shown in FIG. 6, the content of APG-1252 in HSA-1252 is above 99% during the storage at all the two tempretures. No new impurity was found in the HSA formulation during the period. The content of BMS-1244 was slightly increased in 4° C. with less than 0.5%. For clinical-1252, a new impurity (impurity 9) was found during the period. The result indicated both HSA-1252 had a slightly higher hydrolysis rate compared to clinical-1252, but still remained in acceptable range for at least 13 months. However, clinical-1252 introduces a new impurity due to the drug and expients reaction, which may induce potential risk in patients.

Example VII

This example describes the materials and methods for Example VIII and IX.

Hematological Toxicity of HSA-1252 Comparing to Clinical Used Formulation

Experiments next tested the platelet toxicity of HSA-1252 compared to clinical used formulation (Clinical-1252). CD-1 mice (female, 6-8 weeks, Charles River) were iv injected with two formulations and the amount of 1252 was set as 10, 50, 100 mg/Kg. After 1, 4, 24 hours and 7 days of administration, whole blood was collected and tested for hematology analysis. The smear staining of mice blood after 4 h and 24 h dosing both formulations at the dose of 50 mg/kg were conducted to observe the platelet number.

The Interation Between APG-1252 and Albumin

SYBYL software was used to simulate the interaction between APG-1252 and albumin. High docking value (13.47) represent very strong binding ability of APG-1252 to albumin.

The Dilution Stability of HSA-1252 Formulation

The HSA-1252 lyophilization powder was suspended with sodium chloride injections (0.9%) for a drug concentration of 10 mg/ml. Then dilute the suspension for 5, 50, 500, 5000 times. The size distribution was measured immediately after dilution by dynamic light scattering (DLS).

The Stability of HSA-1252 in Medium Mimic Physiological Condition

In order to mimic the dilution of formulation in physiological condition, the resuspended HSA-1252 (with sodium chloride injections) were diluted 5,000 fold in 5% HSA. Nanosight (NS300) analysis was utilized to monitor the size distribution and particle concentration change for the formulation in plasma. Different time points were also detected to analyze the kinetics of nanoparticles in plasma.

The In Vitro Test for Drug Hydrolysis Essays

In order to test if HSA-1252 could delay the hydrolysis of APG-1252 to BMS-1244, two different formulations were incubated in mice plasma and rotated at 37° C. with speed of 100 rpm. At different time point, a small amount of plasma was collected and mixed with acetonitrile to extract free drug from protein. After sonication and centrifugation, supernatant was collected to analyze the percentage of 1244 in different groups.

The Pharmacokinetics Study to Measure the Drug Circulation Time

HSA-1252 and clinical formulation were administered to mice (CD-1, female, n=5) by iv injection at the dose of 50 mg/kg. Blood was collection at different time points (0.5 h, 2 h, 4 h, 8 h, 24 h and 48 h) and the drug conc. (both 1252 and 1244) in blood and plasma was detected by LC-MS.

The In Vitro Platelet Uptake

Nano formulation of 1252 could also decrease the platelet toxicity by preventing its uptake of drug. Therefore, two formulation groups were incubated with plasma for different time points. Platelet was then separated according to the published step, and the drug conc. in the platelet was detected using LC-MS.

Example VIII

This example demonstrates that the albumin nanoformulation of APG-1252 reduces the platelet toxicity of APG-1252 by the special property of albumin nanoparticle.

Figure 7:
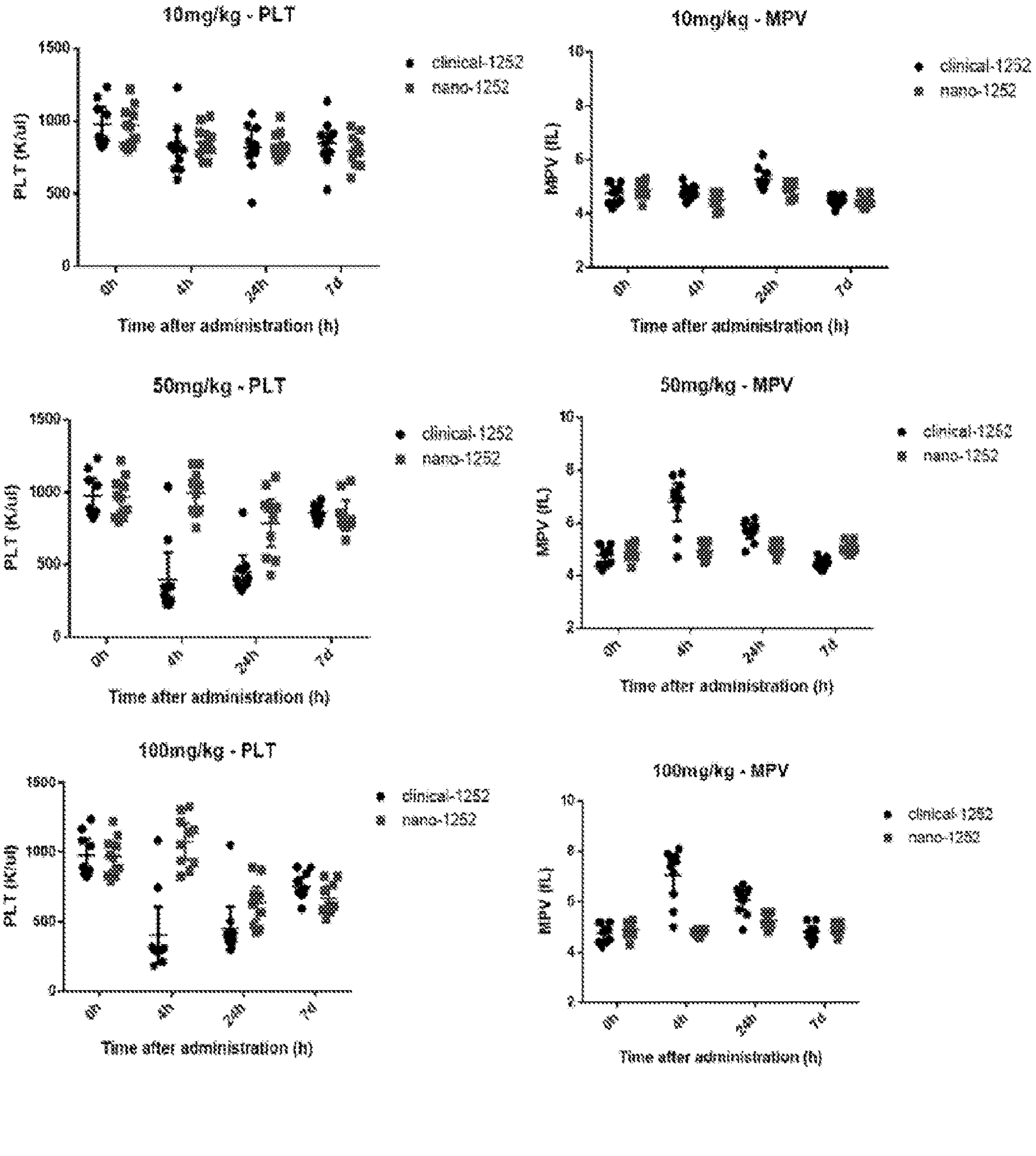
FIG. 7. Platelet toxicity of HSA-1252 and clinical formulation. The platelet count and mean platelet volume (MPV) of mice after dosing clinical-1252 and nano-1252 at different dose: 10 mg/kg, 50 mg/kg and 100 mg/kg.

HSA-1252 Rescued the Platelet Toxicity of 1252 Compared to Clinic Used Formulation As shown in FIG. 7, at the low dose of 10 mg/kg for both formulation, apparent platelet toxicity was not observed. However, when dose was incread to 50 mg/Kg, significant decreas of platelet number was observed at clinical formulation as early as 4 h after administration, and this phenomenon continues at least 24 h. HSA formulation showed better platelet safety under this dose, and only a slight decrease of platelet was observed at 24 h after administration. No significant volume change of platelet was observed for HSA formulation throughout the whole study. This protection of platelet for HSA formulation was also discovered under 100 mg/Kg dosage, which exhibited that HSA-1252 could successfully rescue the platelet toxicity of APG-1252.

Figure 8:
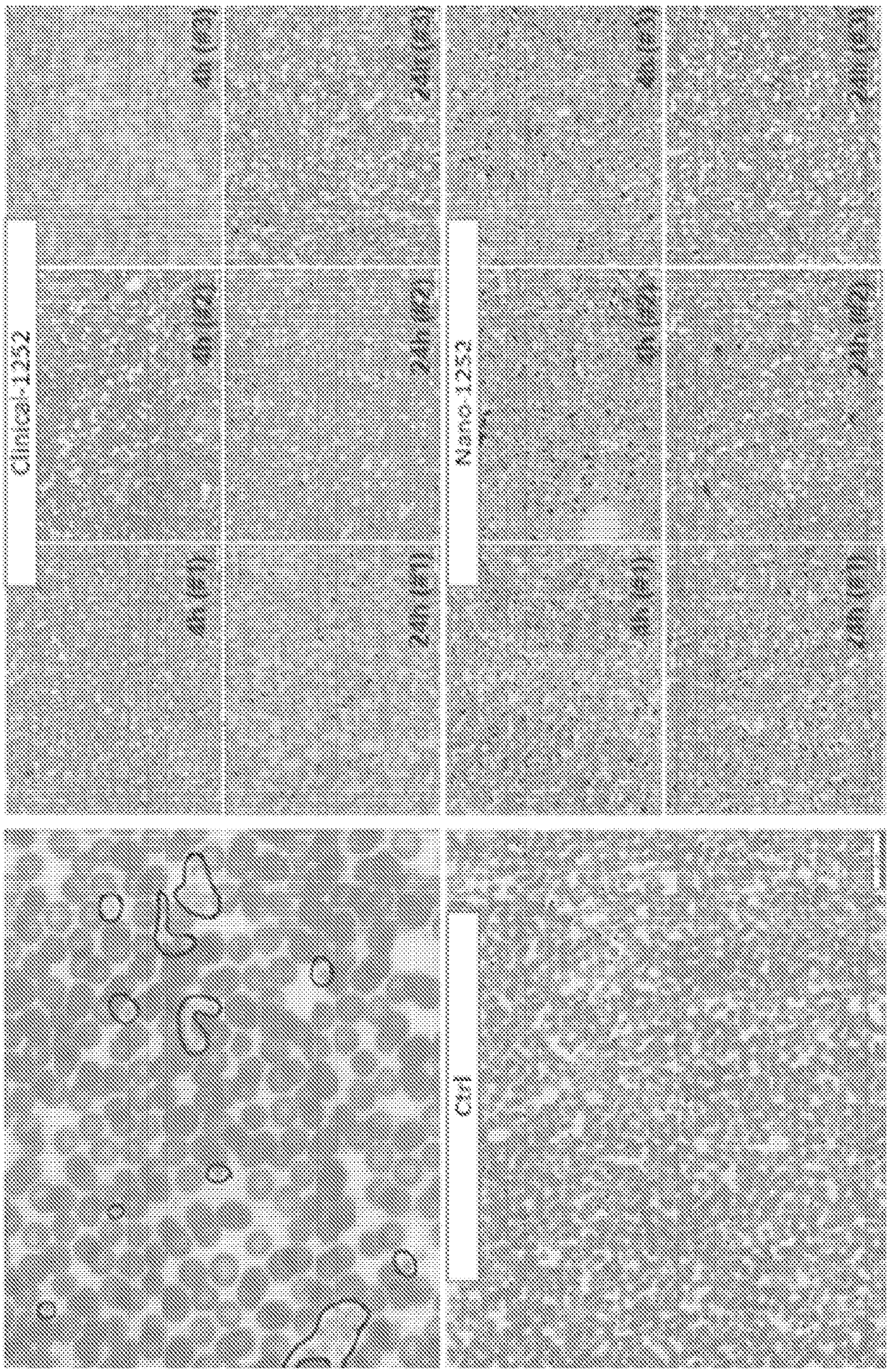
FIG. 8. The hematoxylin and eosin(H&E) staining of mice blood after dosing clinical-1252 and nano-1252 at different dose: 10 mg/kg, 50 mg/kg and 100 mg/kg. The circles and dark dots shows the platelet.
Figure 9:
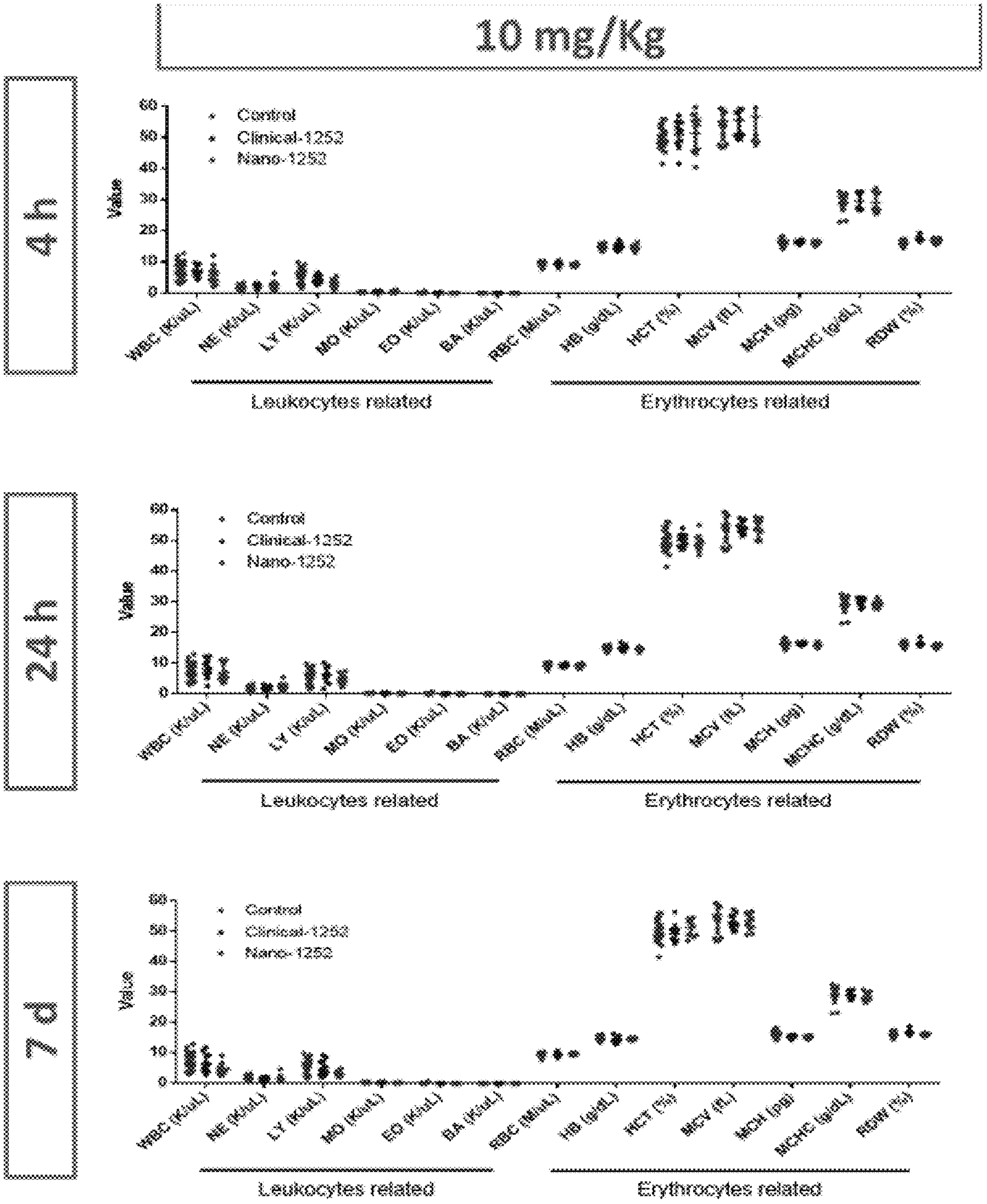
FIG. 9. The hematology results of mice blood after dosing clinical-1252 and nano-1252 at different dose: 10 mg/kg, 50 mg/kg and 100 mg/kg.
Figure 9:
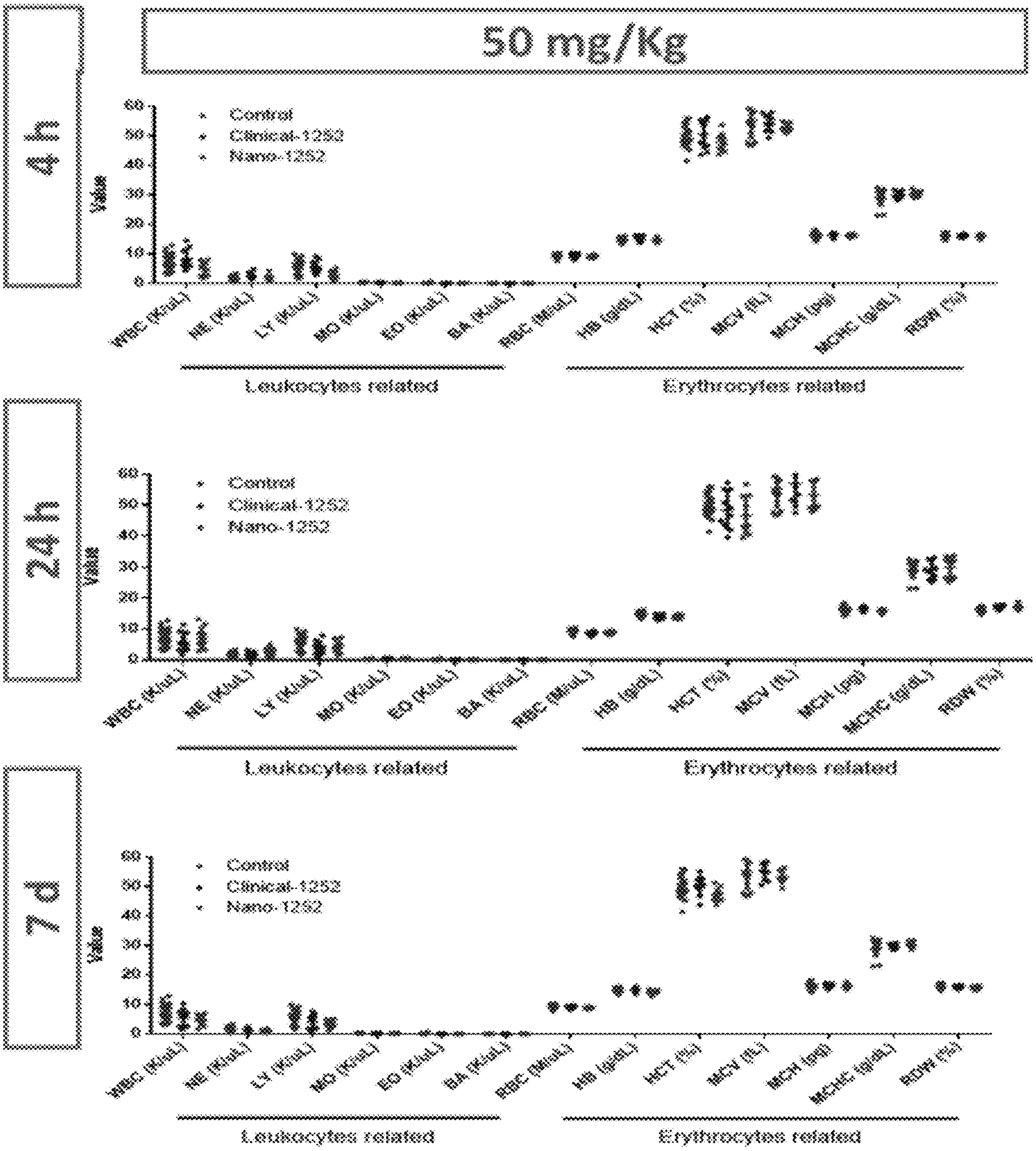
Figure 9:
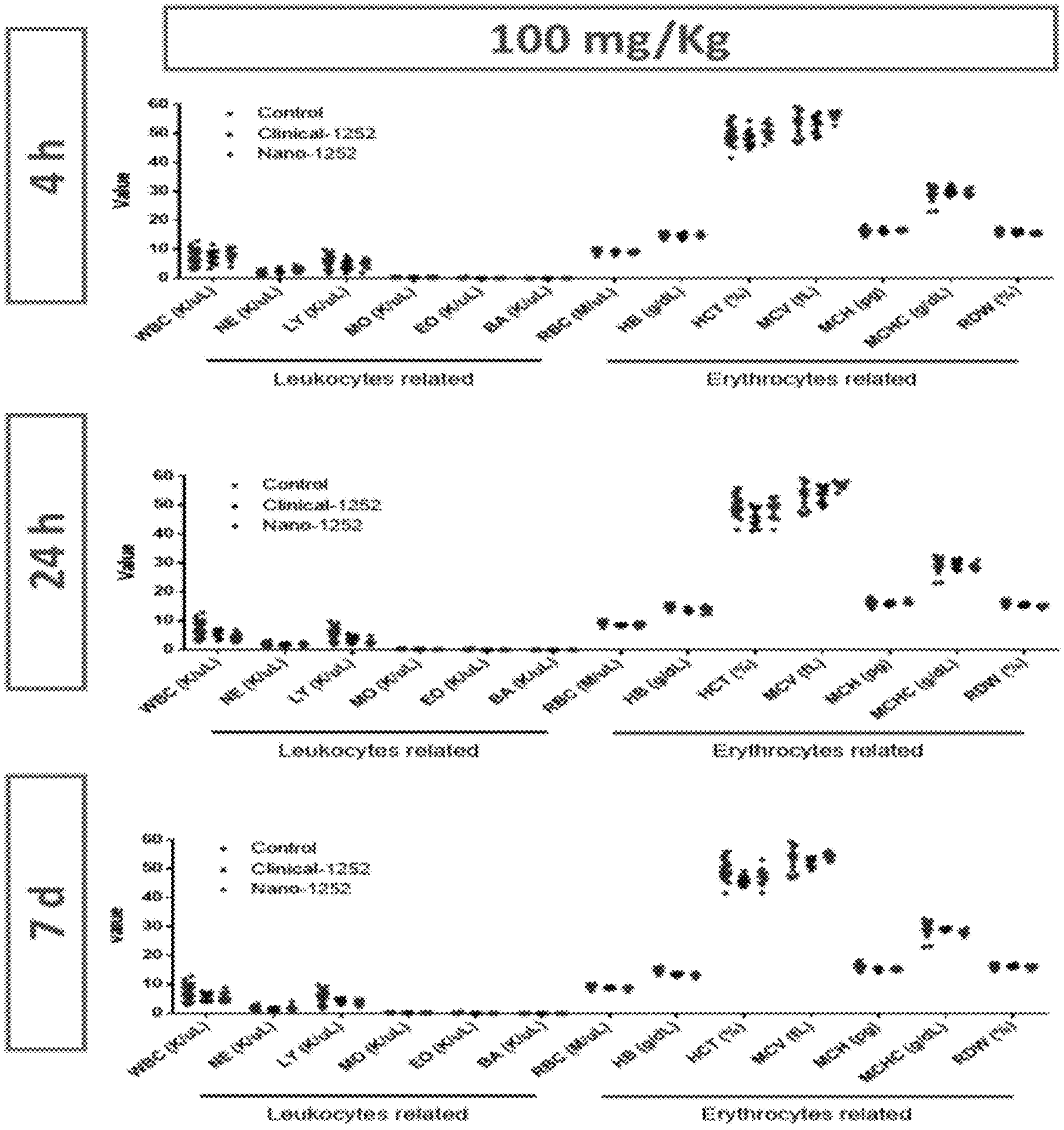

Smear blood staining as shown in FIG. 8 confirmed the platelet toxicity observed by hematological analysis. After administrating both formulations at 50 mg/Kg, 3 blood samples from each group were randomly selected and stained at 4 h and 24 h time points. Platelet in the slides was labeled by red pot to be easily observed. For clinical formulation at 4 h, significantly decrease of platelet was observed, which was only slightly improved after 24 h. However, no obviously change of platelets in HSA formulation was shown at 4 h. Only one slide at 24 h (#3) demonstrated decreased platelets, which was still better than any slides in cinical formulation group. In order to compare the other blood toxicities of these two formulations, leukocytes and erythrocytes-related parameters were also observed for different dosage (10 mg/Kg, 50 mg/Kg and 100 mg/Kg) at different time points (4 h, 24 h, and 7 d). As shown in FIG. 9, no significant difference was observed between these two formulations, demonstrating HSA formulation behaved similarly as clinical formulation in other blood cells.

The APG-1252 has a Strong Interaction with Albumin

Figure 10:
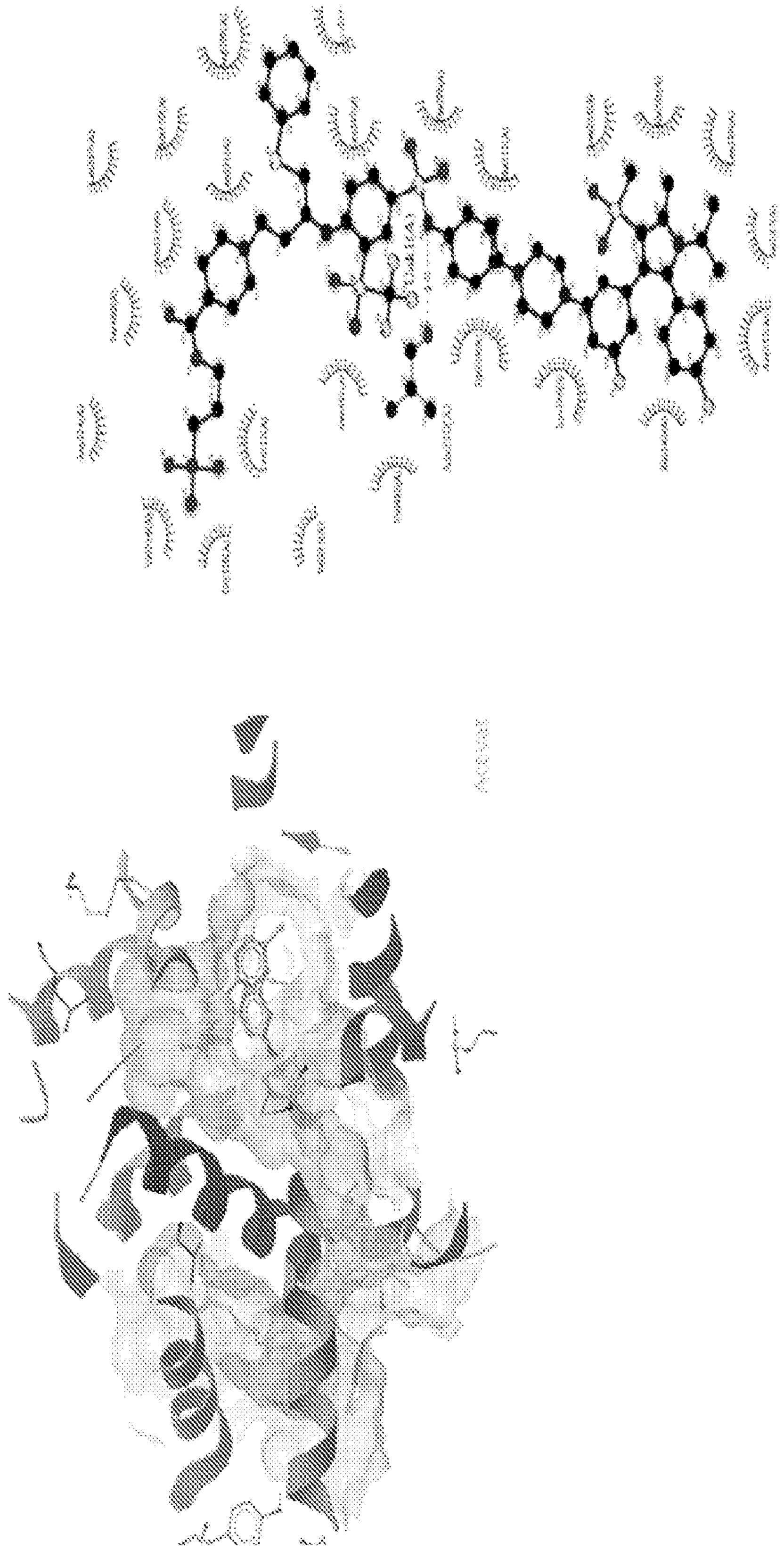
FIG. 10. The interaction of APG-1252 with albumin FIG. 11. The size distribution of HSA-1252 after 5 to 5000 dilution folds.

Nano formulation showed significantly better platelet toxicity compared with clinical formulation (see, FIG. 10). It was hypothesized that albmin might form a stable shell outside of drug core, which can remain stable and prevent the release of drug in circulation. As a result, we first calculate the interaction of APG-1252 with albumin. According to the SYBYL software simulation, APG-1252 has a cLog P of 8.35, which indicates a very high lypophilicity. APG-1252 has a strong interaction with albumin. The docking value is 13.47.

HSA-1252 Remains Stable after Dilution

Figure 11:
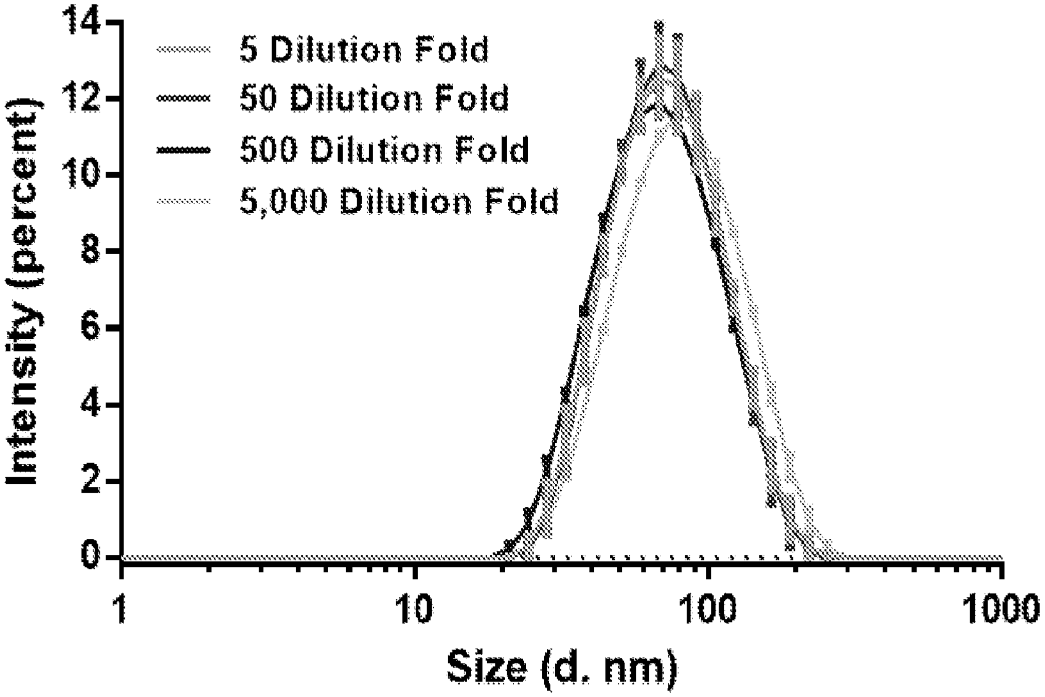

Nanoparticle will be diluted in after i.v injection. The dilution stability is tested here to ensure the albumin nanoparticle remaining stable in circulation. As shown in FIG. 11, the size of HSA-1252 kept consistent after 5 to 5000 dilution folds.

HSA-1252 Remains Stable while Traveling with Blood

Figure 12:
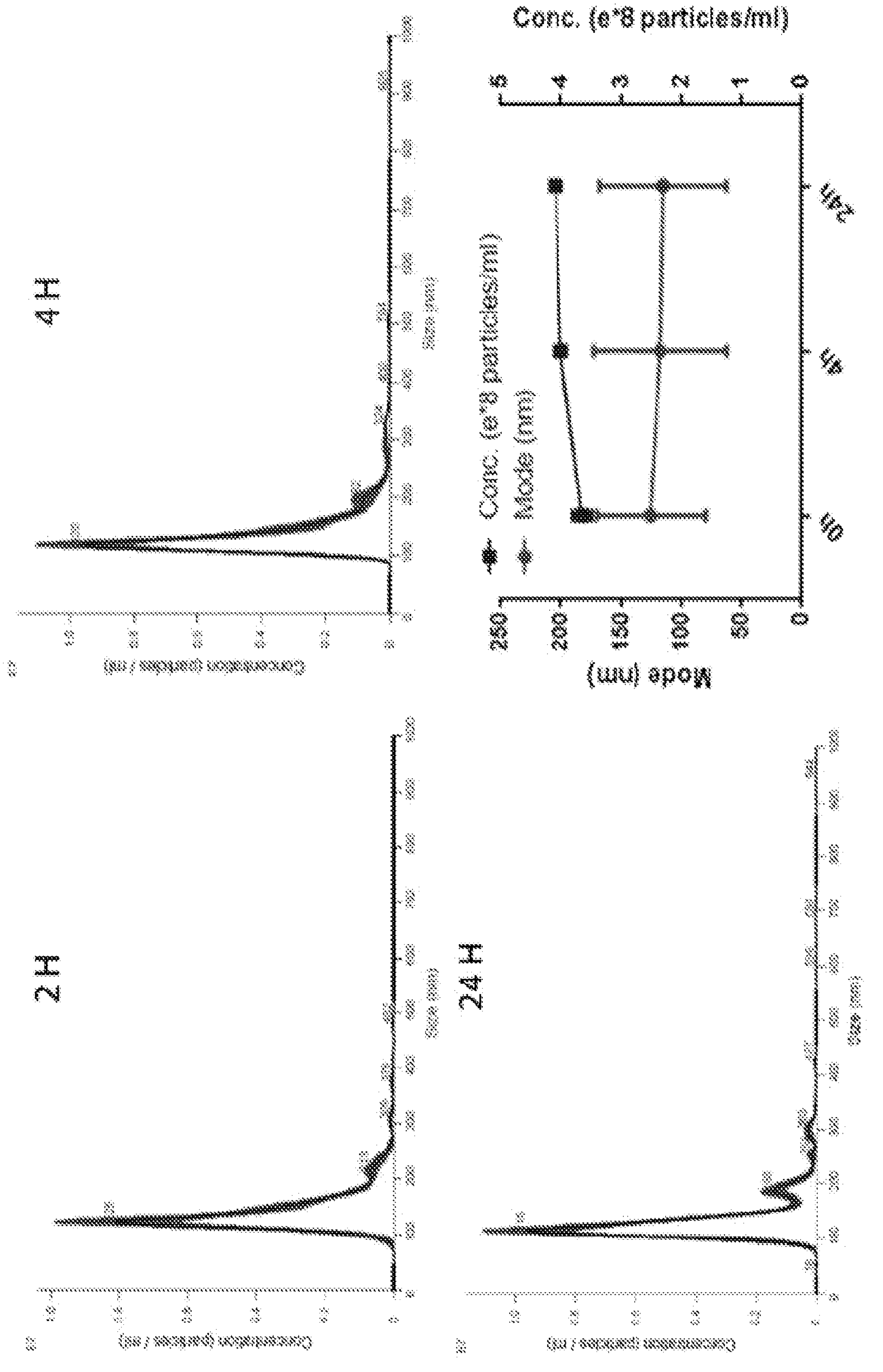
FIG. 12. The size distribution of HSA-1252 in physiological conditions up to 24 hours.

After injection, HSA-1252 particle travels with blood and gradually distribute in tissues. To test if the nanoparticle travel integrated rather than dissociated in circulation, experiments were conducted that incubated HSA-1252 in 5% HSA medium and shaking at 37 degree. As shown in the FIG. 12, the HSA-1252 shows strong stability in physiological condition up to 24 h. The mode size from different time points was around 100 nm and showed no significant change along the incubation time. Interestingly, the particle concentration didn't change along with the time, confirming a hypothesis that the nanoparticle didn't dissociation or aggregation in physiological conditions.

In Vitro Test for Drug Hydrolysis Essays

Figure 13:
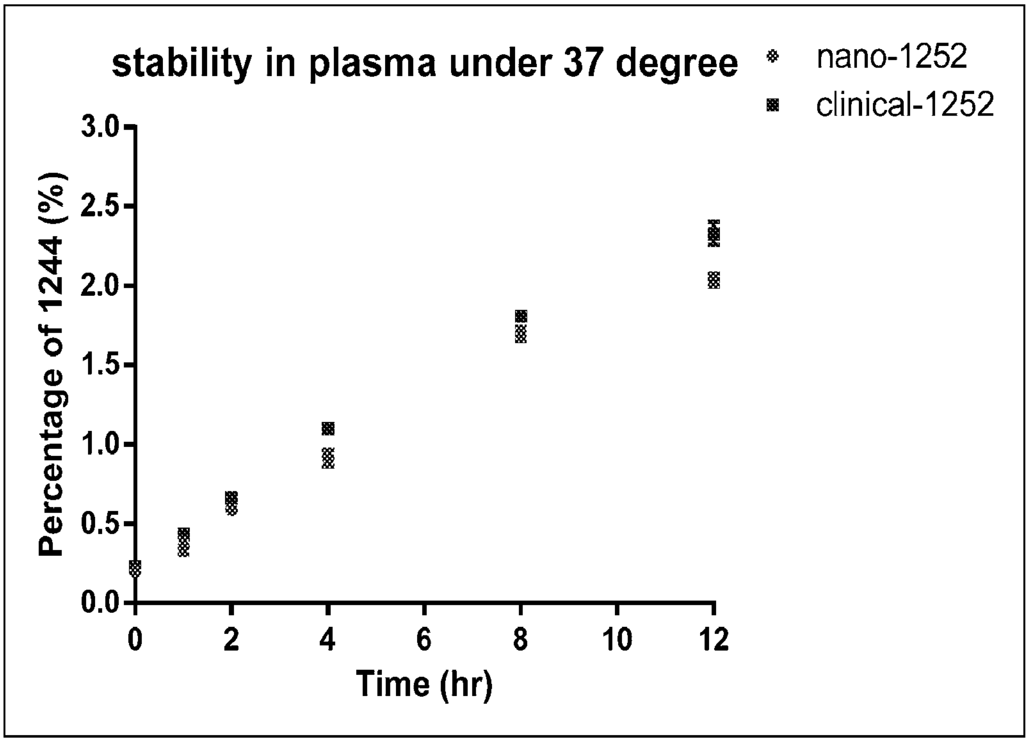
FIG. 13. The in vitro hydrolysis of APG-1252 of HSA-1252 and clinical-1252 in plasma under 37 degree.

Nano formulation showed significantly better platelet toxicity compared with clinical formulation (see, FIG. 13). It was hypothesized that one possible reason might be due to the delayed hydrolysis of 1244 for nano formulation. HSA-1252 slowed down the hydrolysis of 1252 to 1244 in 4 degree. However, there is a slight decrease of 1244% in nano group comparing to clinical used formulation for 12 hours under physiological condition (serum, 37 degree, shaking at 100 rpm).

In Vivo Pharmcokinetics

Figure 14:
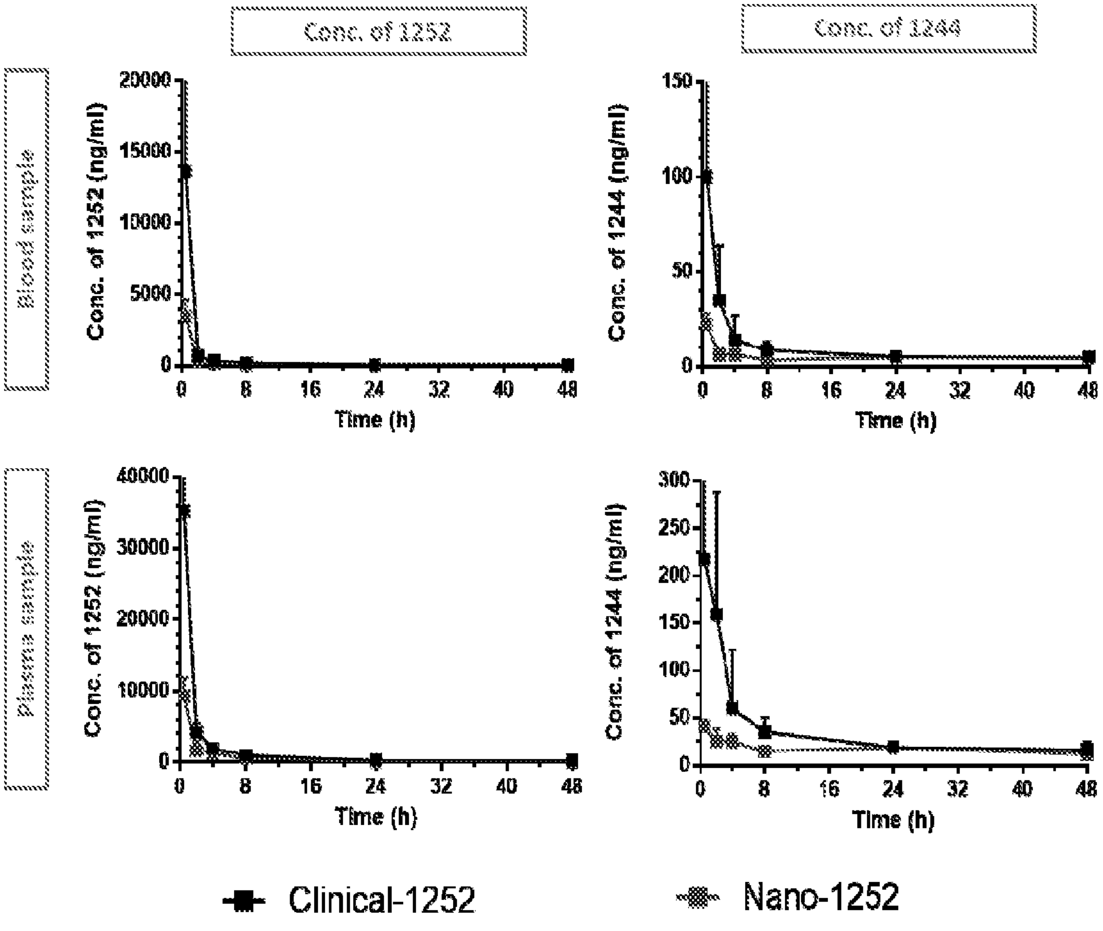
FIG. 14. The APG-1252 and BMS-1244 plasma concentration versus time curve. Mice were dosed with nano-1252 or clinical-1252.

Another hypothesis is that albumin formulation reduces the APG-1252 and BMS-1244 concentration in blood. As shown in FIG. 14, the distribution of APG-1252 in blood was significantly faster in HSA formulation compared to clinical formulation. For each time point, 2-5 times lower of concentration was observed in HSA formulation comparing to clinical used formulation. Similarly, the active compound in this nano-formulation, BMS-1244, was also much lower in both blood and plasma samples.

CONCLUSIONS

HSA-1252 formulation demonstrated strong stability both in vitro and in vivo. Different from Abraxene, which is the albumin formulation of paclitaxel and easily dissipated after 150-200 fold dilution, HSA-1252 was stable even after 5,000 fold dilution and kept the structure in plasma up to 24 hours. HSA-1252 showed no obvious platelet depletion at the conc of 50 mg/Kg, while clinic used formulation induce significant platelet depletion. This enhancement was possibly due to the decreased platelet uptake or blood retention time of the 1252 and the reduced hydrolysis of the drug. Hence, HSA-1252 was proved to be able to rescue the platelet toxicity of APG-1252, which in further could enhance the therapy window of this drug and reach better efficacy.

Example IX

The albumin homeostasis recycling is mediated by the neonatal Fc receptor (FcRn), thus the tissue distribution of albumin nanoparticle is impacted by FcRn, which is widely expressed across many cell types. The clinic used albumin formulation Abraxane® achieved similar concentration with paclitaxel (TAXOL®) in the pancreas and lung, while the tissue/plasma ratios of ABRAXANE® was significantly higher in pancreas and lung than paclitaxel, which correlated with ABRAXANE®'s superior efficacy to treat pancreatic cancer and lung cancer in comparison with paclitaxel (TAXOL®). In comparison with paclitaxel, GENEXOL PM® did not show superior efficacy in a phase III clinical trials to paclitaxel. Our previous data indeed showed that GENEXOL PM® did not improve tissue/plasma ratios in pancreas, lung, or breast, which explain the clinical data (see, Different nanoformulations alter the tissue distribution of paclitaxel, which aligns with reported distinct efficacy and safety profiles. Li F et al. Mol. Pharm. 2018). These results suggest that albumin nanoparticle can improve the tissue/plasma ratios of encapsulated drugs in pancreas, lung cancer and metastasis breast cancer (lung is the major metastasis organ), thus improve the efficacy of drug in these three cancers. Now the clinical trial of APG-1252 is focus on lung cancer. It is hypothesized that albumin nanoparticle will further increase the efficacy of drug in lung cancer, pancreas cancer and metastasis breast cancer. To prove the hypothesis, experiments will be conducted to test the in vivo tissue distribution to study the difference of tissue distribution of HSA-1252 formulation and clinical used formulation. The in vivo efficacy study to test if HSA-1252 can improve the efficacy of 1252 in pancreas cancer, lung cancer and metastasis breast cancer will also be tested.

Figure 15:
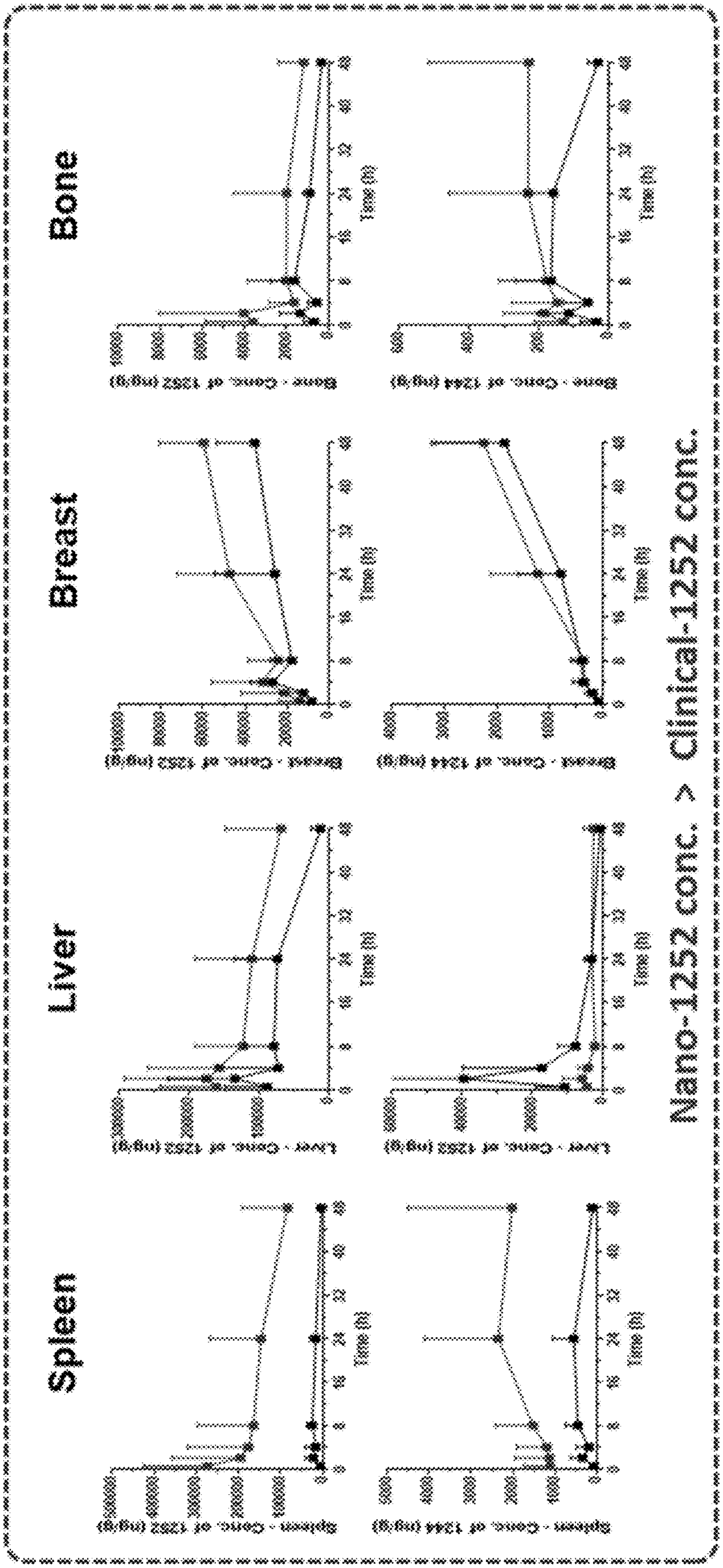
FIG. 15. The APG-1252 and BMS-1244 concentration versus time curve in different tissues in CD-1 IGS mice. Mice were dosed with nano-1252 or clinical-1252.
Figure 15:
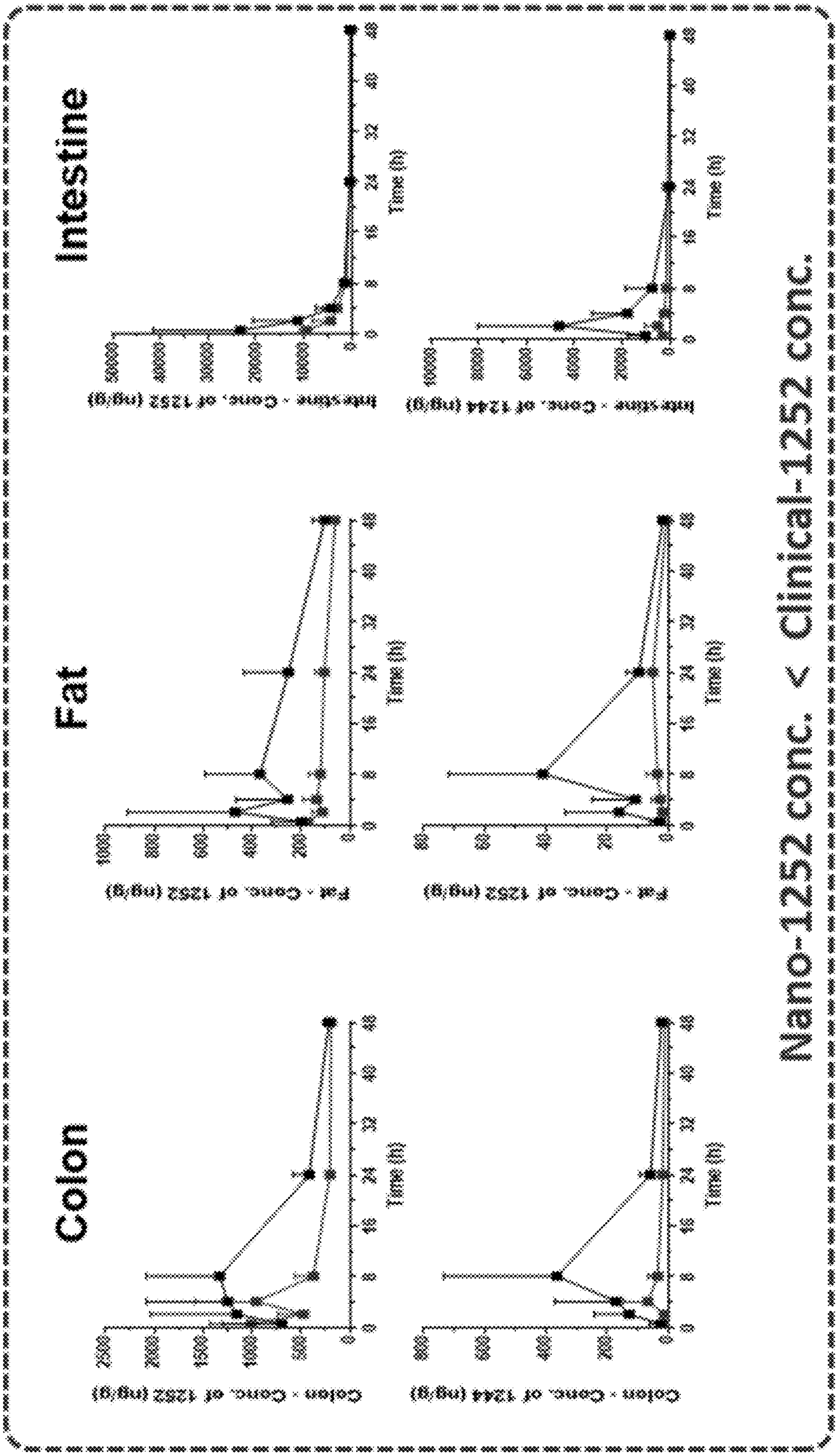
Figure 15:
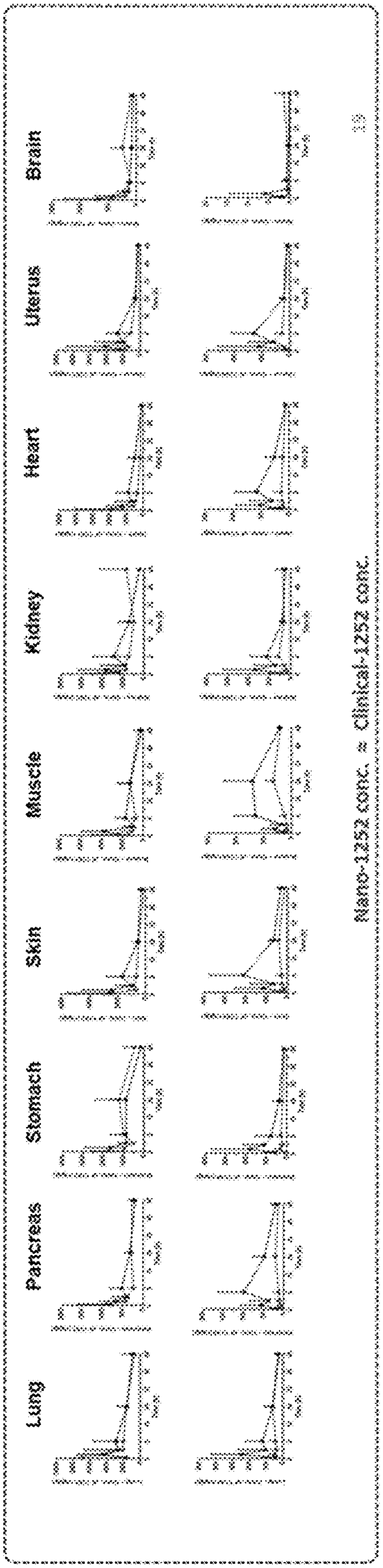
Figure 15:
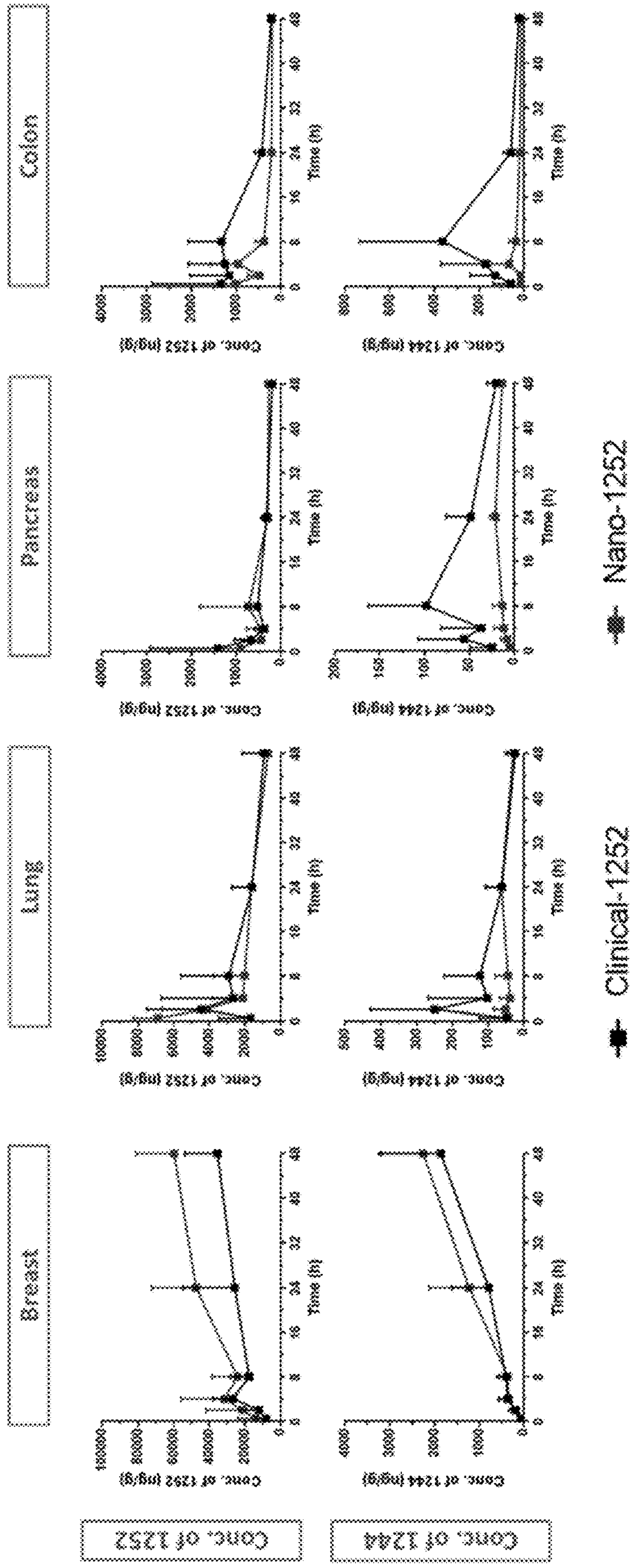
Figure 16:
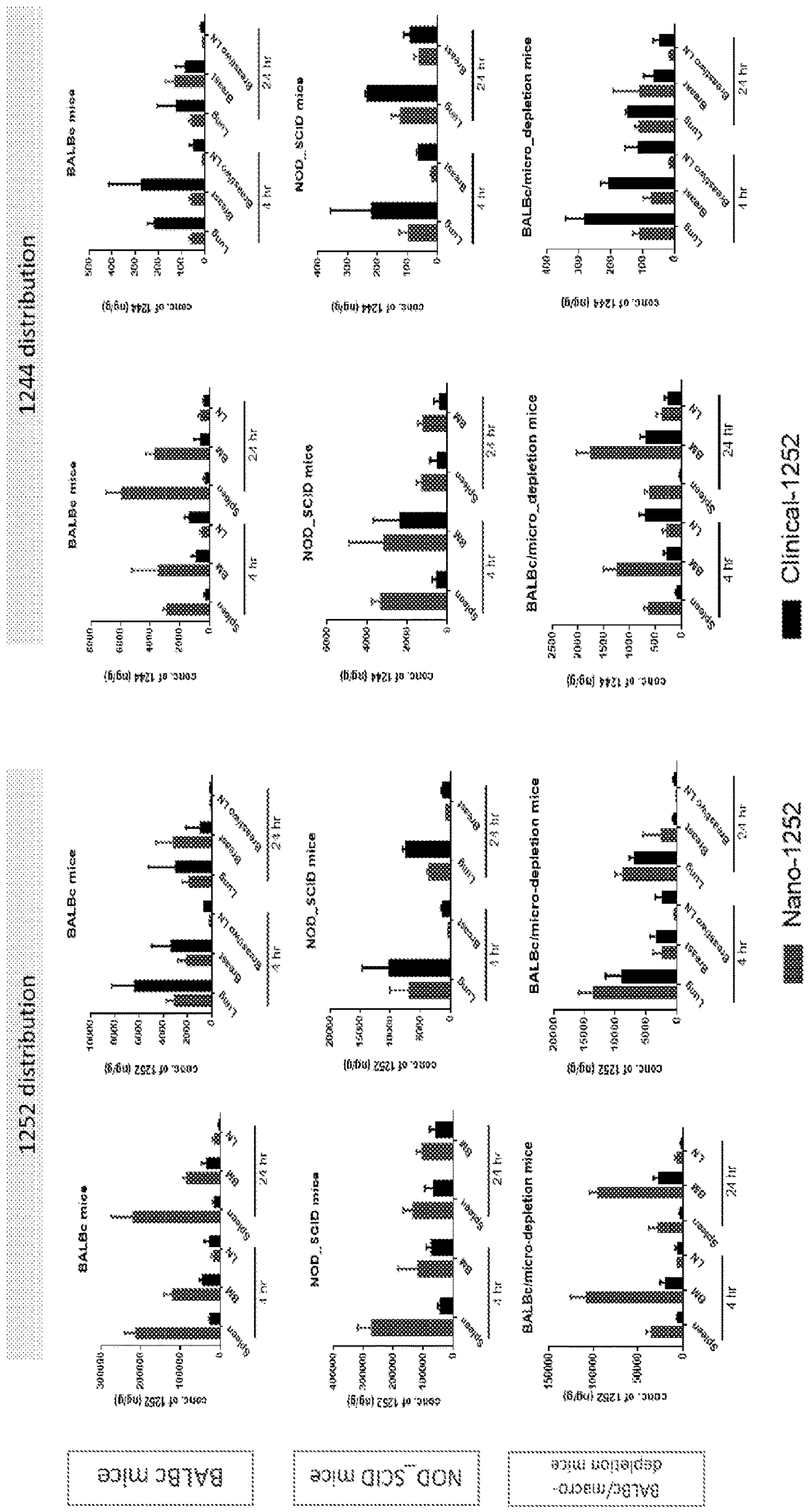
FIG. 16. The APG-1252 and BMS-1244 concentration versus time curve in bone marrow, spleen and lymph node in different types of mice (BALB/c, NOD_SCID mice and BALBc/macro-depletion mice).

As shown in FIG. 15, the nano-1252 was able to increase the APG-1252 accumulation in breast for 2 times, and its hydrolisis product BMS-1244 for 1-1.5 times. This special property of nanoformulation may lead to the improved efficacy of the drug in breast cancer. To be metioned, BMS-1244 is less than 10% of APG-1252 for 48 hours, thus only APG-1252 concentration is considered to be related to efficacy.

On the other hand, nano-1252 decreased the accumulation in colon, which may releated to the lower toxcicity in colon.

Example X

This example describes the cytotoxicity of HSA-1252 and APG-1252.

The cytotoxicity of HSA-1252 and APG-1252 were compared in different cancer cell lines. Cells were seeded in a 96 well plate with 3000 cells per well and culture for 24 h, the appropriate amount of drug in a serial dilution manner was added to each well. After incubation for 72 h, Cell Proliferation was detected by CellTiter 96™ AQueous Nonradioactive Cell Proliferation Assay Kit.

Figure 17:
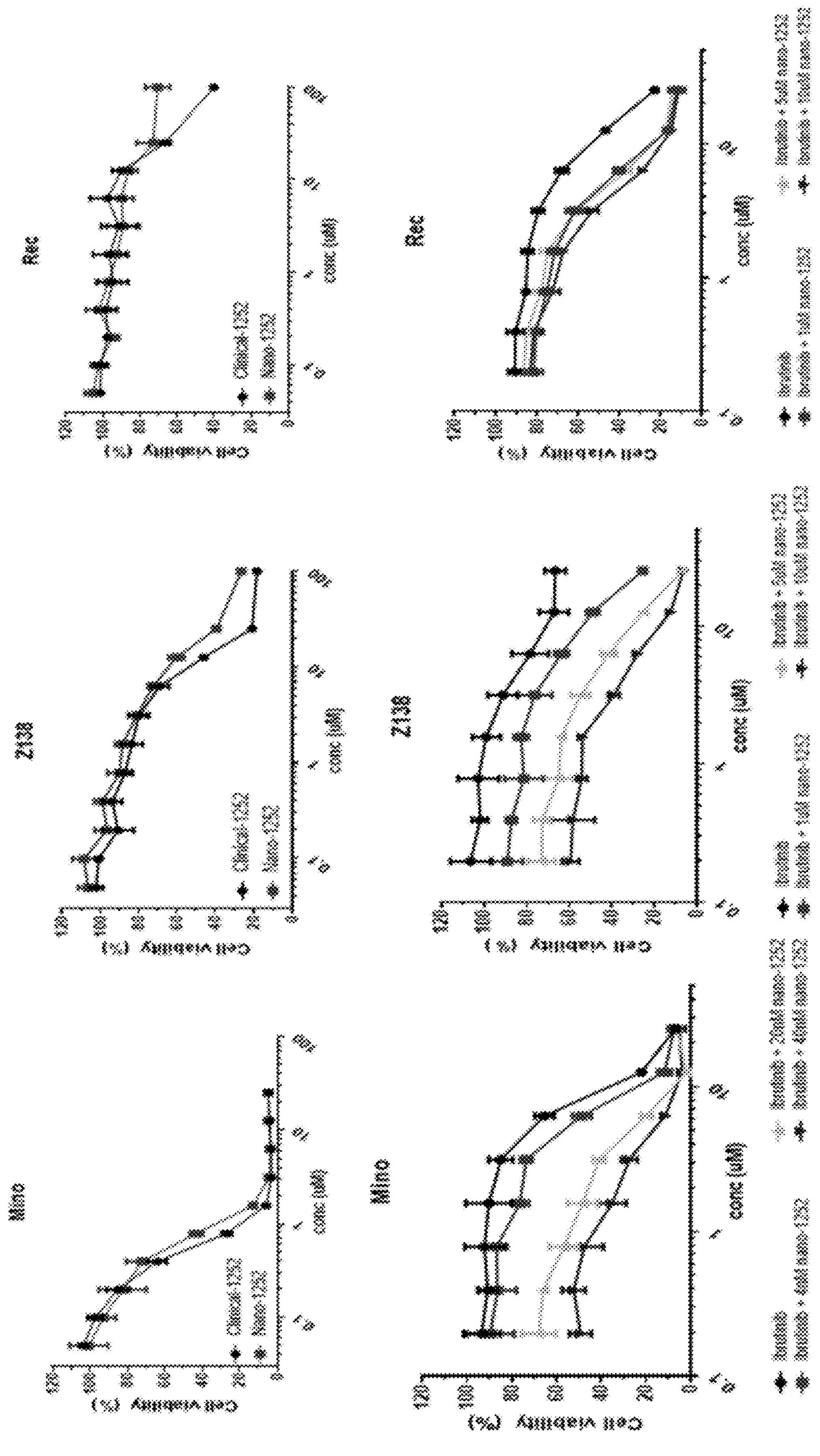
FIG. 17. The cytotoxicity of HSA-1252 and APG-1252 (single drug) or in combine with Ibrutinib against mantle cell lymphoma (B cell non-Hodgkin's lymphoma) cell line Mino, and Z138 and Rec.

The cytotoxicity of HSA-1252 and APG-1252 alone or in combine with Ibrutinib was tested against mantle cell lymphoma (B cell non-Hodgkin's lymphoma) cell line Mino, and Z138 and Rec. As shown in FIG. 17, the cytotoxicity of HSA-1252 and APG-1252 alone in the three cell lines are similar. Ibrutinib was the first line therapy in lymphoma and leukemia in clinic, but its efficacy is limited by accuquired drug resistantance. The combination of HSA-1252 with Ibrutinib greatly increased the cytotoxicity.

Figure 18:
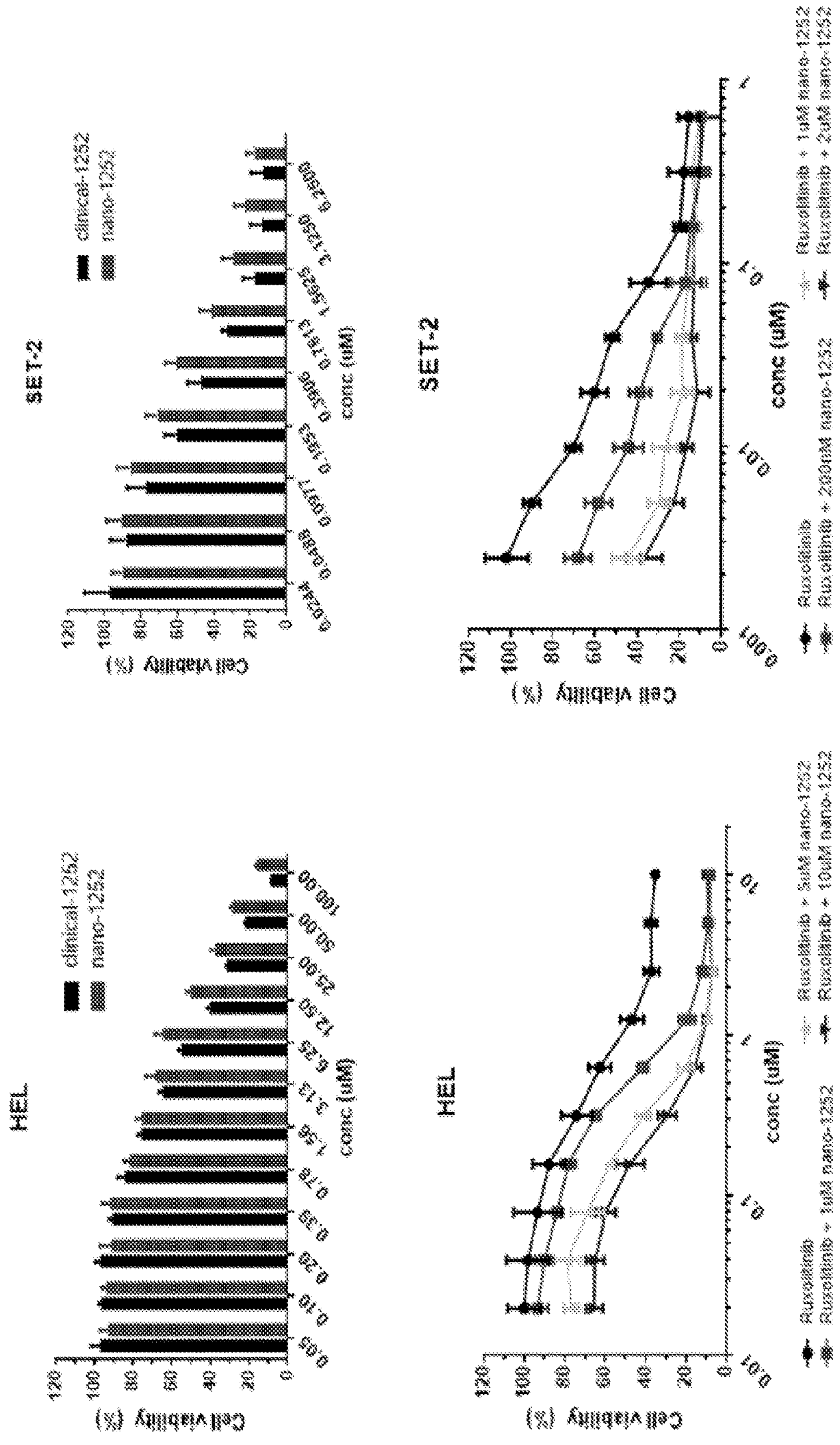
FIG. 18. The cytotoxicity of HSA-1252 and APG-1252 (single drug) or in combine with Ibrutinib against erythroleukemic HEL, megakaryoblastic leukemic SET-2 and Ruxolitinib resistant HEL cell line.
Figure 18:
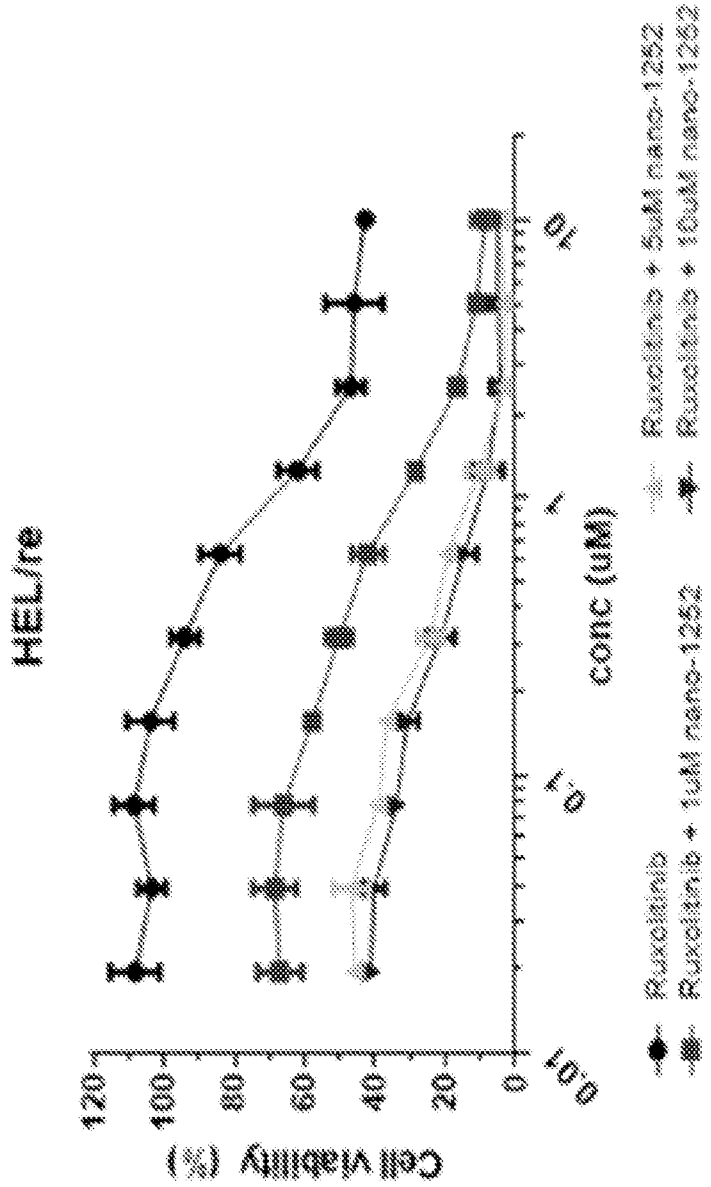
Figure 19:
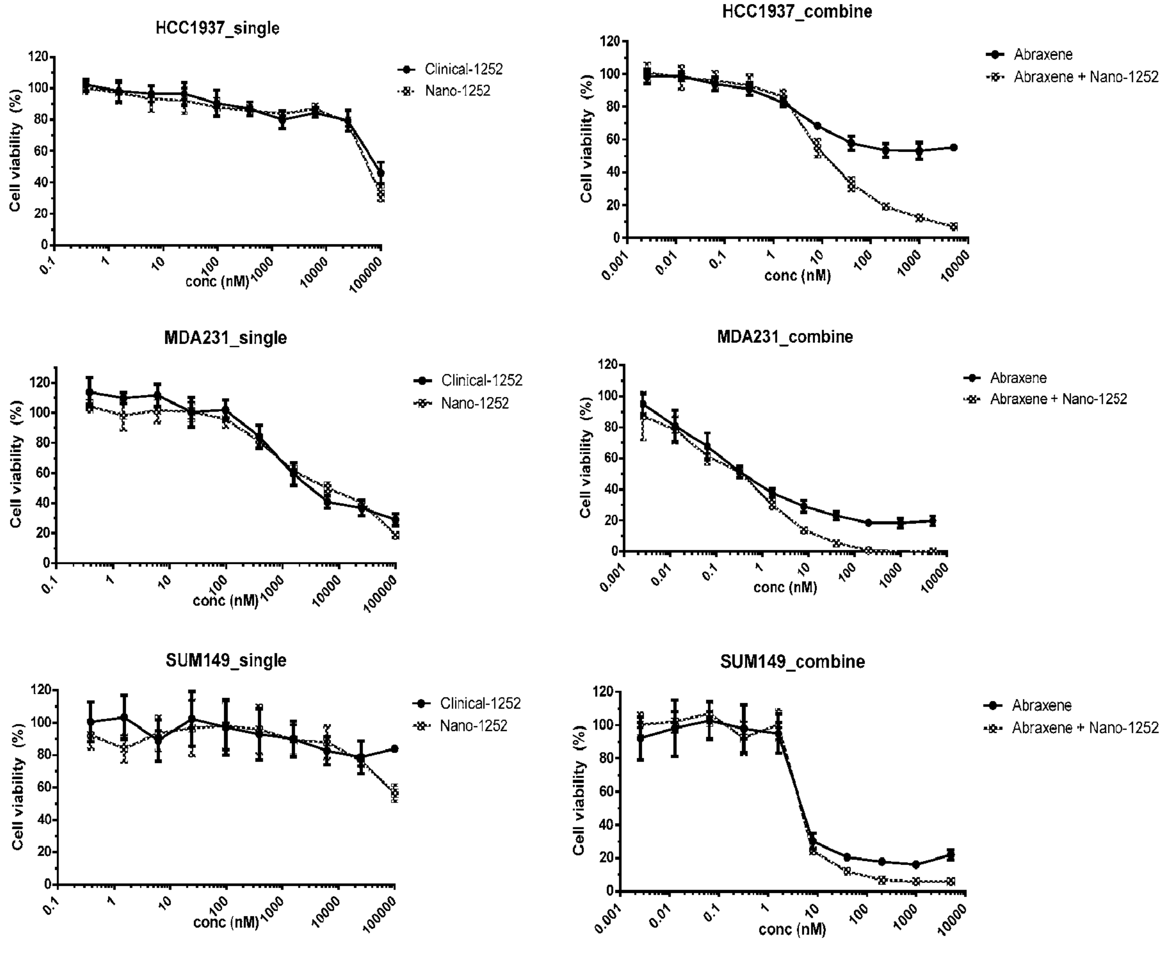
FIG. 19. The cytotoxicity of HSA-1252 and APG-1252 (single drug) or in combine with ABRAXANE® against breast cancer cell (HCC1937, MDA-231, SUM149).

The cytotoxicity of HSA-1252 and APG-1252 (single drug) or in combine with Ibrutinib was also tested on erythroleukemic HEL, megakaryoblastic leukemic SET-2 and Ruxolitinib resistant HEL cell line. As shown in FIG. 18, the cytotoxicity of HSA-1252 and APG-1252 alone in HEL and SET-2 cell lines are similar. The combination of HSA-1252 with Ibrutinib greatly increased the cytotoxicity in all three cell lines.

The cytotoxicity of HSA-1252 and APG-1252 were compared in breast cancer cell lines HCC-1937, MDA-231 and SUM149. As shown in FIG. 18, HSA-1252 showed similar efficacy compared to free drug, which demonstrated that the nanoformulation did not change the efficacy of APG-1252. Furthermore, HSA-1252 increased the cytotoxicity of chemotherapeutic drug ABRAXANE® in all the three cell lines.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A composition comprising a nanoparticle comprising APG-1252

(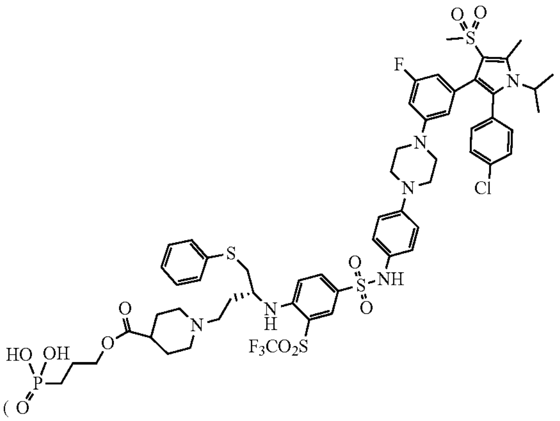)

non-covalently bound to albumin;

wherein the albumin-APG-1252 nanoparticle maintains a particle size of less than 100 nm after at least a 5,000-fold dilution in plasma, wherein the albumin-APG-1252 nanoparticle is capable of reducing platelet toxicity in plasma compared to free APG-1252, and wherein, upon intravenous administration, the albumin-APG-1252 nanoparticle yields at least a 2-fold higher concentration of APG-1252 in bone marrow and lymph nodes relative to free APG-1252 at 24 hours post-dose.

2. The composition of claim 1, wherein the composition is capable of inhibiting Bcl-2 and Bcl-xL protein activity in cancerous cells.

3. The composition of claim 1, wherein the nanoparticle is further associated with an antigen.

4. The composition of claim 1, wherein the nanoformulation is capable of reducing the platelet toxicity of APG-1252 by the following mechanisms (1) reduce concentration in the blood circulation, (2) decrease platelet uptake, (3) protect premature degradation of APG-1252 in circulation.

5. A method of treating a subject diagnosed as having breast cancer and/or a hematological tumor arising from bone marrow comprising administering a pharmaceutically effective amount of the composition of claim 1 to the subject, thereby treating the breast cancer and/or a hematological tumor arising from bone marrow.

6. The method of claim 5, wherein the composition is co-administered with a chemotherapeutic agent selected from aldesleukin, altretamine, amifostine, asparaginase, bleomycin, capecitabine, carboplatin, carmustine, cladribine, cisapride, cisplatin, cyclophosphamide, cytarabine, dacarbazine, dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel, pilocarpine, prochloroperazine, rituximab, paclitaxel tamoxifen, paclitaxel, topotecan hydrochloride, trastuzumab, vinblastine, vincristine and vinorelbine tartrate.

* * * * *